(12) United States Patent
Satish et al.

(10) Patent No.: US 11,670,143 B2
(45) Date of Patent: Jun. 6, 2023

(54) METHOD FOR ESTIMATING A QUANTITY OF A BLOOD COMPONENT IN A FLUID RECEIVER AND CORRESPONDING ERROR

(71) Applicant: Gauss Surgical, Inc., Menlo Park, CA (US)

(72) Inventors: Siddarth Satish, Redwood City, CA (US); Andrew T. Hosford, Idaho Falls, ID (US); Kevin J. Miller, Mountain View, CA (US); Milton McColl, Los Altos Hills, CA (US); Juan Carlos Aragon, Los Altos, CA (US)

(73) Assignee: Gauss Surgical, Inc., Menlo Park, CA (US)

( * ) Notice: Subject to any disclaimer, the term of this patent is extended or adjusted under 35 U.S.C. 154(b) by 61 days.

(21) Appl. No.: 17/175,897

(22) Filed: Feb. 15, 2021

(65) Prior Publication Data

US 2021/0192917 A1 Jun. 24, 2021

Related U.S. Application Data

(60) Continuation of application No. 16/545,159, filed on Aug. 20, 2019, now Pat. No. 10,957,179, which is a (Continued)

(51) Int. Cl.
*G06T 7/62* (2017.01)
*G08B 21/02* (2006.01)
(Continued)

(52) U.S. Cl.
CPC ............ *G08B 21/0272* (2013.01); *A61B 5/02* (2013.01); *A61B 5/02042* (2013.01);
(Continued)

(58) Field of Classification Search
None
See application file for complete search history.

(56) References Cited

U.S. PATENT DOCUMENTS 2,707,955 A 5/1955 Borden
3,182,252 A 5/1965 Den
(Continued)

FOREIGN PATENT DOCUMENTS

CA 2870635 A1 10/2013
CN 101505813 A 8/2009
(Continued)

OTHER PUBLICATIONS

"European Application Serial No. 19156549.8, Response filed Oct. 12, 2021 to Communication Pursuant to Article 94(3) EPC dated Jun. 11, 2021", 17 pgs.
(Continued)

*Primary Examiner* — Anand P Bhatnagar
(74) *Attorney, Agent, or Firm* — Howard & Howard Attorneys PLLC

(57) ABSTRACT

A method and system for communicating estimated blood loss parameters of a patient to a user, the method comprising: receiving data representative of an image, of a fluid receiver; automatically detecting a region within the image associated with a volume of fluid received at the fluid receiver, the volume of fluid including a blood component; calculating an estimated amount of the blood component present in the volume of fluid based upon a color parameter represented in the region, and determining a bias error associated with the estimated amount of the blood component; updating an analysis of an aggregate amount of the blood component and an aggregate bias error associated with blood loss of the patient, based upon the estimated amount of the blood component and the bias error; and providing information from the analysis of the aggregate
(Continued)

amount of the blood component and the aggregate bias error, to the user.

20 Claims, 15 Drawing Sheets

Related U.S. Application Data continuation of application No. 15/861,389, filed on Jan. 3, 2018, now Pat. No. 10,426,356, which is a division of application No. 14/687,860, filed on Apr. 15, 2015, now Pat. No. 9,870,625, which is a continuation-in-part of application No. 13/544,646, filed on Jul. 9, 2012, now Pat. No. 8,792,693.

(60) Provisional application No. 61/980,026, filed on Apr. 15, 2014, provisional application No. 61/646,814, filed on May 14, 2012, provisional application No. 61/646,818, filed on May 14, 2012, provisional application No. 61/506,082, filed on Jul. 9, 2011.

(51) Int. Cl.

| | |
|---|---|
| *H04W 4/021* | (2018.01) |
| *H04W 4/80* | (2018.01) |
| *H04W 4/029* | (2018.01) |
| *G08B 13/14* | (2006.01) |
| *H04W 4/02* | (2018.01) |
| *H04W 4/20* | (2018.01) |
| *A61B 5/02* | (2006.01) |
| *H04W 8/00* | (2009.01) |
| *G06V 10/25* | (2022.01) |
| *G06V 40/16* | (2022.01) |
| *G06V 10/24* | (2022.01) |
| *G06F 3/0488* | (2022.01) |
| *G06K 7/00* | (2006.01) |
| *G06K 7/08* | (2006.01) |
| *G06K 7/10* | (2006.01) |
| *G06K 19/06* | (2006.01) |
| *G06K 19/07* | (2006.01) |
| *G06K 19/073* | (2006.01) |
| *G06K 19/077* | (2006.01) |
| *G06K 19/08* | (2006.01) |
| *G06Q 20/18* | (2012.01) |
| *G06Q 20/20* | (2012.01) |
| *G06Q 20/34* | (2012.01) |
| *G06Q 20/38* | (2012.01) |
| *G06Q 20/40* | (2012.01) |
| *G06Q 30/0207* | (2023.01) |
| *G06Q 30/0241* | (2023.01) |
| *G06Q 30/0601* | (2023.01) |
| *G07F 7/08* | (2006.01) |
| *G07F 7/10* | (2006.01) |
| *G08B 25/01* | (2006.01) |
| *G08B 5/22* | (2006.01) |
| *H04W 84/18* | (2009.01) |

(52) U.S. Cl.
CPC ......... *G06F 3/0488* (2013.01); *G06K 7/0004* (2013.01); *G06K 7/084* (2013.01); *G06K 7/087* (2013.01); *G06K 7/10297* (2013.01); *G06K 19/06187* (2013.01); *G06K 19/06206* (2013.01); *G06K 19/07* (2013.01); *G06K 19/0702* (2013.01); *G06K 19/0704* (2013.01); *G06K 19/0723* (2013.01); *G06K 19/0725* (2013.01); *G06K 19/0775* (2013.01); *G06K 19/07345* (2013.01); *G06K 19/07703* (2013.01); *G06K 19/07705* (2013.01); *G06K 19/07707* (2013.01); *G06K 19/07709* (2013.01); *G06K 19/07749* (2013.01); *G06K 19/07766* (2013.01); *G06K 19/07769* (2013.01); *G06K 19/07773* (2013.01); *G06K 19/083* (2013.01); *G06Q 20/18* (2013.01); *G06Q 20/20* (2013.01); *G06Q 20/34* (2013.01); *G06Q 20/341* (2013.01); *G06Q 20/3415* (2013.01); *G06Q 20/352* (2013.01); *G06Q 20/385* (2013.01); *G06Q 20/401* (2013.01); *G06Q 30/0222* (2013.01); *G06Q 30/0241* (2013.01); *G06Q 30/0277* (2013.01); *G06Q 30/0641* (2013.01); *G06T 7/62* (2017.01); *G06V 10/24* (2022.01); *G06V 10/25* (2022.01); *G06V 40/172* (2022.01); *G07F 7/0806* (2013.01); *G07F 7/1008* (2013.01); *G08B 13/1427* (2013.01); *G08B 21/0244* (2013.01); *G08B 21/0247* (2013.01); *G08B 21/0269* (2013.01); *G08B 21/0277* (2013.01); *H04W 4/02* (2013.01); *H04W 4/021* (2013.01); *H04W 4/029* (2018.02); *H04W 4/20* (2013.01); *H04W 4/80* (2018.02); *H04W 8/005* (2013.01); *G06T 2207/10024* (2013.01); *G06T 2207/30004* (2013.01); *G06V 2201/03* (2022.01); *G08B 5/22* (2013.01); *G08B 25/016* (2013.01); *H04W 84/18* (2013.01)

(56) References Cited

U.S. PATENT DOCUMENTS

| | | |
|---|---|---|
| 3,199,507 A | 8/1965 | Kamm |
| 3,367,431 A | 2/1968 | Prindie |
| 3,646,938 A | 3/1972 | Haswell |
| 3,832,135 A | 8/1974 | Drozdowski et al. |
| 3,864,571 A | 2/1975 | Stillman et al. |
| 3,948,390 A | 4/1976 | Ferreri |
| 4,105,019 A | 8/1978 | Haswell |
| 4,149,537 A | 4/1979 | Haswell |
| 4,190,153 A | 2/1980 | Olsen |
| 4,244,369 A | 1/1981 | Mcavinn et al. |
| 4,295,537 A | 10/1981 | Mcavinn et al. |
| 4,313,292 A | 2/1982 | Mcwilllams |
| 4,402,373 A | 9/1983 | Comeau |
| 4,422,548 A | 12/1983 | Cheesman et al. |
| 4,429,789 A | 2/1984 | Puckett, Jr. |
| 4,562,842 A | 1/1986 | Morfeid et al. |
| 4,583,546 A | 4/1986 | Garde |
| 4,642,089 A | 2/1987 | Zupkas et al. |
| 4,681,571 A | 7/1987 | Nehring |
| 4,773,423 A | 9/1988 | Hakky |
| 4,784,267 A | 11/1988 | Gessler et al. |
| 4,832,198 A | 5/1989 | Alikhan |
| 4,917,694 A | 4/1990 | Jessup |
| 4,922,922 A | 5/1990 | Pollock et al. |
| 5,009,275 A | 4/1991 | Sheehan |
| 5,029,584 A | 7/1991 | Smith |
| 5,031,642 A | 7/1991 | Nosek |
| 5,048,683 A | 9/1991 | Westlake |
| 5,119,814 A | 6/1992 | Minnich |
| 5,132,087 A | 7/1992 | Kristen et al. |
| 5,190,059 A | 3/1993 | Fabian et al. |
| 5,227,765 A | 7/1993 | Ishizuka et al. |
| 5,231,032 A | 7/1993 | Ludvigsen |
| 5,236,664 A | 8/1993 | Ludvigsen |
| 5,285,682 A | 2/1994 | Mickiish |
| 5,348,533 A | 9/1994 | Papillon et al. |
| 5,369,713 A | 11/1994 | Schwartz et al. |
| 5,443,082 A | 8/1995 | Mewbum |
| 5,492,537 A | 2/1996 | Vancaillie |
| 5,522,805 A | 6/1996 | Vancaillie et al. |
| 5,629,498 A | 5/1997 | Pollock et al. |

(56) References Cited

U.S. PATENT DOCUMENTS

| | | |
|---|---|---|
| 5,633,166 A | 5/1997 | Westgard et al. |
| 5,650,596 A | 7/1997 | Morris et al. |
| 5,709,670 A | 1/1998 | Vancaillie et al. |
| 5,807,358 A | 9/1998 | Herweck et al. |
| 5,851,835 A | 12/1998 | Groner |
| 5,923,001 A | 7/1999 | Morris et al. |
| 5,931,824 A | 8/1999 | Stewart et al. |
| 5,934,278 A | 8/1999 | Ishihara et al. |
| 5,944,668 A | 8/1999 | Vancaillie et al. |
| 5,956,130 A | 9/1999 | Vancaillie et al. |
| 5,984,893 A | 11/1999 | Ward |
| 5,996,889 A | 12/1999 | Fuchs et al. |
| 6,006,119 A | 12/1999 | Soller et al. |
| 6,061,583 A * | 5/2000 | Ishihara ............... A61B 5/6826 600/476 |
| 6,063,051 A | 5/2000 | Stern |
| 6,104,939 A | 8/2000 | Groner et al. |
| 6,359,683 B1 | 3/2002 | Berndt |
| 6,510,330 B1 | 1/2003 | Enejder |
| 6,640,130 B1 | 10/2003 | Freeman et al. |
| 6,641,039 B2 | 11/2003 | Southard |
| 6,699,231 B1 | 3/2004 | Sterman et al. |
| 6,728,561 B2 | 4/2004 | Smith et al. |
| 6,730,054 B2 | 5/2004 | Pierce et al. |
| 6,763,148 B1 | 7/2004 | Sternberg et al. |
| 6,777,623 B2 | 8/2004 | Ballard |
| 6,781,067 B2 | 8/2004 | Montagnino et al. |
| 6,998,541 B2 | 2/2006 | Morris et al. |
| 7,001,366 B2 | 2/2006 | Ballard |
| 7,112,273 B2 | 9/2006 | Weigel et al. |
| 7,147,626 B2 | 12/2006 | Goodman et al. |
| 7,158,030 B2 | 1/2007 | Chung |
| 7,180,014 B2 | 2/2007 | Farber et al. |
| 7,255,003 B2 | 8/2007 | Schnelter |
| 7,274,947 B2 | 9/2007 | Koo et al. |
| 7,277,570 B2 | 10/2007 | Armstrong |
| 7,297,834 B1 | 11/2007 | Shapiro |
| 7,299,981 B2 | 11/2007 | Hickle |
| 7,364,545 B2 * | 4/2008 | Klein ............... G01N 33/4905 600/300 |
| 7,384,399 B2 | 6/2008 | Ghajar |
| 7,430,047 B2 | 9/2008 | Budd et al. |
| 7,430,478 B2 | 9/2008 | Fletcher-haynes et al. |
| 7,469,727 B2 | 12/2008 | Marshall |
| 7,499,581 B2 | 3/2009 | Tribble et al. |
| 7,557,710 B2 | 7/2009 | Sanchez et al. |
| 7,641,612 B1 | 1/2010 | Mccall |
| D611,731 S | 3/2010 | Levine |
| 7,670,289 B1 | 3/2010 | Mccall |
| 7,703,674 B2 | 4/2010 | Stewart et al. |
| 7,708,700 B2 | 5/2010 | Ghajar |
| 7,711,403 B2 * | 5/2010 | Jay ..................... A61B 5/0059 600/407 |
| 7,749,217 B2 | 7/2010 | Podhajsky |
| 7,795,491 B2 | 9/2010 | Stewart et al. |
| 7,819,818 B2 | 10/2010 | Ghajar |
| 7,872,201 B1 | 1/2011 | Whitney |
| 7,909,806 B2 | 3/2011 | Goodman et al. |
| 7,966,269 B2 | 6/2011 | Bauer et al. |
| 7,995,816 B2 | 8/2011 | Roger et al. |
| 8,025,173 B2 | 9/2011 | Michaels |
| 8,105,296 B2 | 1/2012 | Morris et al. |
| 8,181,860 B2 | 5/2012 | Fleck et al. |
| 8,194,235 B2 * | 6/2012 | Kosaka ............ G01N 35/00584 356/244 |
| 8,241,238 B2 | 8/2012 | Hiruma et al. |
| 8,279,068 B2 | 10/2012 | Morris et al. |
| 8,310,658 B2 * | 11/2012 | Wardlaw ............... G06T 7/0012 382/134 |
| 8,374,397 B2 | 2/2013 | Shpunt et al. |
| 8,398,546 B2 | 3/2013 | Pacione et al. |
| 8,472,693 B2 | 6/2013 | Davis et al. |
| 8,479,989 B2 | 7/2013 | Fleck et al. |
| 8,576,076 B2 | 11/2013 | Morris et al. |
| 8,626,268 B2 | 1/2014 | Adler et al. |
| 8,639,226 B2 | 1/2014 | Hutchings et al. |
| 8,693,753 B2 | 4/2014 | Nakamura |
| 8,704,178 B1 | 4/2014 | Pollock et al. |
| 8,768,014 B2 | 7/2014 | Du et al. |
| 8,792,693 B2 | 7/2014 | Satish et al. |
| 8,823,778 B2 | 9/2014 | Tian et al. |
| 8,897,523 B2 | 11/2014 | Satish et al. |
| 8,983,167 B2 | 3/2015 | Satish et al. |
| 8,985,446 B2 | 3/2015 | Fleck et al. |
| 9,047,663 B2 | 6/2015 | Satish et al. |
| 9,171,368 B2 | 10/2015 | Satish et al. |
| 9,347,817 B2 | 5/2016 | Pollock et al. |
| 9,595,104 B2 | 3/2017 | Satish et al. |
| 9,646,375 B2 | 5/2017 | Satish et al. |
| 9,652,655 B2 | 5/2017 | Satish et al. |
| 9,773,320 B2 | 9/2017 | Satish et al. |
| 9,824,441 B2 | 11/2017 | Satish et al. |
| 9,870,625 B2 | 1/2018 | Satish et al. |
| 9,936,906 B2 | 4/2018 | Satish et al. |
| 10,282,839 B2 | 5/2019 | Satish et al. |
| 10,426,356 B2 | 10/2019 | Satish et al. |
| 10,528,782 B2 | 1/2020 | Satish et al. |
| 10,706,541 B2 | 7/2020 | Satish et al. |
| 10,957,179 B2 | 3/2021 | Satish et al. |
| 2003/0069509 A1 | 4/2003 | Matzinger et al. |
| 2003/0095197 A1 | 5/2003 | Wheeler et al. |
| 2003/0130596 A1 | 7/2003 | Goltz |
| 2004/0024295 A1 | 2/2004 | Cook et al. |
| 2004/0031626 A1 | 2/2004 | Morris et al. |
| 2004/0129678 A1 | 7/2004 | Crowley et al. |
| 2005/0051466 A1 | 3/2005 | Carter et al. |
| 2005/0163354 A1 | 7/2005 | Ziegler |
| 2005/0265996 A1 | 12/2005 | Lentz |
| 2006/0058593 A1 | 3/2006 | Drinan et al. |
| 2006/0178578 A1 | 8/2006 | Tribble |
| 2006/0224086 A1 | 10/2006 | Harty |
| 2007/0004959 A1 | 1/2007 | Carrier et al. |
| 2007/0024946 A1 | 2/2007 | Panasyuk et al. |
| 2007/0108129 A1 | 5/2007 | Mori et al. |
| 2007/0243137 A1 | 10/2007 | Hainfeld et al. |
| 2007/0287182 A1 | 12/2007 | Morris et al. |
| 2008/0029416 A1 | 2/2008 | Paxton |
| 2008/0030303 A1 | 2/2008 | Kobren et al. |
| 2008/0045845 A1 | 2/2008 | Pfeiffer et al. |
| 2008/0194906 A1 | 8/2008 | Mahony et al. |
| 2009/0076470 A1 | 3/2009 | Ryan |
| 2009/0080757 A1 | 3/2009 | Roger et al. |
| 2009/0257632 A1 | 10/2009 | Lalpuria et al. |
| 2009/0310123 A1 * | 12/2009 | Thomson ............... G01N 21/85 356/40 |
| 2009/0317002 A1 | 12/2009 | Dein |
| 2010/0003714 A1 | 1/2010 | Bachur, Jr. et al. |
| 2010/0007727 A1 | 1/2010 | Torre-Bueno |
| 2010/0025336 A1 | 2/2010 | Carter et al. |
| 2010/0027868 A1 | 2/2010 | Kosaka et al. |
| 2010/0066996 A1 | 3/2010 | Kosaka et al. |
| 2010/0081942 A1 * | 4/2010 | Huiku ................... G16H 40/60 600/483 |
| 2010/0087770 A1 * | 4/2010 | Bock ................... A61M 1/3656 604/4.01 |
| 2010/0111384 A1 | 5/2010 | Nagai et al. |
| 2010/0156759 A1 | 6/2010 | Mazur et al. |
| 2010/0280117 A1 | 11/2010 | Patrick et al. |
| 2011/0028850 A1 * | 2/2011 | Schuhrke ............ A61B 5/0261 600/476 |
| 2011/0066182 A1 | 3/2011 | Falus |
| 2011/0118647 A1 | 5/2011 | Paolini et al. |
| 2011/0192745 A1 | 8/2011 | Min |
| 2011/0196321 A1 | 8/2011 | Wudyka |
| 2011/0200239 A1 | 8/2011 | Levine et al. |
| 2011/0275957 A1 | 11/2011 | Bhandari |
| 2011/0305376 A1 | 12/2011 | Neff et al. |
| 2011/0316973 A1 | 12/2011 | Miller et al. |
| 2012/0000297 A1 | 1/2012 | Hashizume et al. |
| 2012/0064132 A1 | 3/2012 | Aizawa et al. |
| 2012/0065482 A1 | 3/2012 | Robinson et al. |
| 2012/0106811 A1 | 5/2012 | Chen et al. |
| 2012/0127290 A1 | 5/2012 | Tojo et al. |

(56) References Cited

U.S. PATENT DOCUMENTS

| | | | |
|---|---|---|---|
| 2012/0195486 A1 | 8/2012 | Levine et al. | |
| 2012/0195489 A1* | 8/2012 | Levine | G01N 33/49 |
| | | | 382/134 |
| 2012/0210778 A1 | 8/2012 | Palmer et al. | |
| 2012/0257188 A1 | 10/2012 | Yan et al. | |
| 2012/0262704 A1 | 10/2012 | Zahniser et al. | |
| 2012/0262705 A1* | 10/2012 | Zahniser | G06V 20/695 |
| | | | 356/40 |
| 2012/0309636 A1 | 12/2012 | Gibbons et al. | |
| 2012/0327365 A1 | 12/2012 | Makihira | |
| 2013/0010094 A1 | 1/2013 | Satish et al. | |
| 2013/0011031 A1 | 1/2013 | Satish et al. | |
| 2013/0011042 A1 | 1/2013 | Satish et al. | |
| 2013/0034908 A1 | 2/2013 | Barstis et al. | |
| 2013/0088354 A1 | 4/2013 | Thomas | |
| 2013/0094996 A1 | 4/2013 | Janssenswiilen | |
| 2013/0170729 A1 | 7/2013 | Wardlaw et al. | |
| 2013/0301901 A1 | 11/2013 | Satish et al. | |
| 2013/0303870 A1 | 11/2013 | Satish et al. | |
| 2013/0308852 A1 | 11/2013 | Hamsici et al. | |
| 2014/0079297 A1 | 3/2014 | Tadayon et al. | |
| 2014/0207091 A1 | 7/2014 | Heagle et al. | |
| 2014/0294237 A1 | 10/2014 | Litvak et al. | |
| 2014/0330094 A1 | 11/2014 | Pacione et al. | |
| 2015/0221088 A1 | 8/2015 | Satish et al. | |
| 2015/0294460 A1 | 10/2015 | Satish et al. | |
| 2015/0310634 A1 | 10/2015 | Babcock et al. | |
| 2015/0339813 A1* | 11/2015 | Zahniser | G06T 7/0012 |
| | | | 348/77 |
| 2016/0027173 A1* | 1/2016 | Satish | G01N 21/90 |
| | | | 382/128 |
| 2016/0069743 A1 | 3/2016 | Mcquilkin et al. | |
| 2016/0123998 A1 | 5/2016 | Macintyre et al. | |
| 2016/0331248 A1 | 11/2016 | Satish et al. | |
| 2016/0331282 A1 | 11/2016 | Satish et al. | |
| 2017/0011276 A1 | 1/2017 | Mehring et al. | |
| 2017/0023446 A1 | 1/2017 | Rietveld et al. | |
| 2017/0186160 A1 | 6/2017 | Satish et al. | |
| 2017/0351894 A1 | 12/2017 | Satish et al. | |
| 2017/0352152 A1 | 12/2017 | Satish et al. | |
| 2018/0199827 A1 | 7/2018 | Satish et al. | |
| 2019/0008427 A1 | 1/2019 | Satish et al. | |
| 2020/0082695 A1 | 3/2020 | Satish et al. | |
| 2020/0104560 A1 | 4/2020 | Satish et al. | |

FOREIGN PATENT DOCUMENTS

| | | |
|---|---|---|
| EP | 2729901 B1 | 9/2016 |
| EP | 3106087 A1 | 12/2016 |
| EP | 3106087 B1 | 2/2019 |
| JP | 59161801 U | 10/1984 |
| JP | S59161801 U | 10/1984 |
| JP | 61176357 A | 8/1986 |
| JP | 62144652 A | 6/1987 |
| JP | S62144652 U | 9/1987 |
| JP | H06510210 A | 11/1994 |
| JP | H07308312 A | 11/1995 |
| JP | 1137845 A | 2/1999 |
| JP | 2000227390 A | 8/2000 |
| JP | 2002331031 A | 11/2002 |
| JP | 2003075436 A | 3/2003 |
| JP | 2005052288 A | 3/2005 |
| JP | 3701031 B2 | 9/2005 |
| JP | 2006280445 A | 10/2006 |
| JP | 2007101482 A | 4/2007 |
| JP | 2008055142 A | 3/2008 |
| JP | 2008519604 A | 6/2008 |
| JP | 2010516429 A | 5/2010 |
| JP | 2011036371 A | 2/2011 |
| JP | 2011515681 A | 5/2011 |
| JP | 2011252804 A | 12/2011 |
| JP | 2014531570 A | 11/2014 |
| JP | 5794597 B2 | 8/2015 |
| WO | WO-9217787 A1 | 10/1992 |
| WO | WO-9639927 A1 | 12/1996 |
| WO | WO-2006053208 A1 | 5/2006 |
| WO | WO-2008094703 A2 | 8/2008 |
| WO | WO-2008094703 A3 | 8/2009 |
| WO | WO-2009117652 A1 | 9/2009 |
| WO | WO-2011019576 A1 | 2/2011 |
| WO | WO-2011145351 A1 | 11/2011 |
| WO | WO-2013009709 A2 | 1/2013 |
| WO | WO-2013138356 A2 | 9/2013 |
| WO | WO-201 3172874 A1 | 11/2013 |
| WO | WO-2013173356 A1 | 11/2013 |
| WO | WO-2013138356 A3 | 12/2013 |
| WO | WO-2014025415 A2 | 2/2014 |
| WO | WO-2013009709 A3 | 5/2014 |
| WO | WO-2014025415 A3 | 6/2015 |
| WO | WO-2015160997 A1 | 10/2015 |
| WO | WO-2015161002 A1 | 10/2015 |

OTHER PUBLICATIONS

"U.S. Appl. No. 13/544,646, Notice of Allowance dated May 12, 2014", 10 pgs.

"U.S. Appl. No. 13/544,646, Preliminary Amendment filed Aug. 15, 2012", 3 pgs.

"U.S. Appl. No. 13/544,664, Final Office Action dated Feb. 12, 2016", 10 pgs.

"U.S. Appl. No. 13/544,664, Non Final Office Action dated Aug. 2, 2016", 7 pgs.

"U.S. Appl. No. 13/544,664, Non Final Office Action dated Aug. 13, 2015", 9 pgs.

"U.S. Appl. No. 13/544,664, Notice of Allowance dated Feb. 15, 2017", 10 pgs.

"U.S. Appl. No. 13/544,664, Preliminary Amendment filed Aug. 15, 2012", 3 pgs.

"U.S. Appl. No. 13/544,664, Response filed Jun. 10, 2016 to Final Office Action dated Feb. 12, 2016", 9 pgs.

"U.S. Appl. No. 13/544,664, Response filed Nov. 12, 2015 to Non Final Office Action dated Aug. 13, 2015", 10 pgs.

"U.S. Appl. No. 13/544,679, Response filed Dec. 2, 2016 to Non Final Office Action dated Aug. 2, 2016", 12 pgs.

"U.S. Appl. No. 13/544,679, Non Final Office Action dated May 9, 2014", 9 pgs.

"U.S. Appl. No. 13/544,679, Notice of Allowance dated Sep. 3, 2014", 8 pgs.

"U.S. Appl. No. 13/544,679, Preliminary Amendment filed Aug. 15, 2012", 3 pgs.

"U.S. Appl. No. 13/544,679, Response filed Aug. 11, 2014 to Non Final Office Action dated May 9, 2014", 13 pgs.

"U.S. Appl. No. 13/738,919, Non Final Office Action dated Sep. 5, 2014", 8 pgs.

"U.S. Appl. No. 13/738,919, Notice of Allowance dated Nov. 10, 2014", 10 pgs.

"U.S. Appl. No. 13/894,054, Final Office Action dated Aug. 26, 2016", 7 pgs.

"U.S. Appl. No. 13/894,054, Non Final Office Action dated Mar. 30, 2016", 9 pgs.

"U.S. Appl. No. 13/894,054, Non Final Office Action dated Apr. 20, 2017", 7 pgs.

"U.S. Appl. No. 13/894,054, Notice of Allowance dated Nov. 20, 2017", 8 pgs.

"U.S. Appl. No. 14/613,807, Non Final Office Action dated Mar. 20, 2015", 8 pgs.

"U.S. Appl. No. 14/687,842, Notice of Allowance dated Jun. 25, 2015", 10 pgs.

"U.S. Appl. No. 14/687,842, Corrected Notice of Allowability dated Sep. 15, 2017", 2 pgs.

"U.S. Appl. No. 14/687,842, Non Final Office Action dated Mar. 24, 2017", 28 pgs.

"U.S. Appl. No. 14/687,842, Notice of Allowance dated Aug. 3, 2017", 9 pgs.

"U.S. Appl. No. 14/687,860, Non Final Office Action dated Nov. 29, 2016", 9 pgs.

(56) References Cited

OTHER PUBLICATIONS

"U.S. Appl. No. 14/687,860, Notice of Allowance dated Apr. 6, 2017", 10 pgs.
"U.S. Appl. No. 14/687,860, Notice of Allowance dated Sep. 27, 2017", 8 pgs.
"U.S. Appl. No. 14/687,860, Response filed Feb. 8, 2017 to Non Final Office Action dated Nov. 29, 2016", 13 pgs.
"U.S. Appl. No. 14/687,860, Response filed Nov. 17, 2016 to Restriction Requirement dated Sep. 21, 2016", 9 pgs.
"U.S. Appl. No. 14/687,860, Restriction Requirement dated Sep. 21, 2016", 6 pgs.
"U.S. Appl. No. 14/876,628, Final Office Action dated Jul. 26, 2016", 5 pgs.
"U.S. Appl. No. 14/876,628, Non Final Office Action dated Dec. 15, 2015", 8 pgs.
"U.S. Appl. No. 14/876,628, Notice of Allowance dated Oct. 26, 2016", 11 pgs.
"Application Serial No. 15/390,017, Non Final Office Action dated Oct. 19, 2018", 12 pgs.
"Application Serial No. 15/390,017, Notice of Allowance dated May 3, 2019", 9 pgs.
"U.S. Appl. No. 15/416,986, Non Final Office Action dated Apr. 11, 2018", 7 pgs.
"U.S. Appl. No. 15/416,986, Notice of Allowability dated Apr. 8, 2019", 4 pgs.
"U.S. Appl. No. 15/416,986, Notice of Allowance dated Jan. 24, 2019", 9 pgs.
"U.S. Appl. No. 15/594,017, Non Final Office Action dated Feb. 21, 2019", 24 pgs.
"U.S. Appl. No. 15/594,017, Notice of Allowance dated Sep. 6, 2019", 11 pgs.
"U.S. Appl. No. 15/594,017, Preliminary Amendment filed Aug. 25, 2017", 6 pgs.
"U.S. Appl. No. 15/594,017, Response filed Jul. 19, 2019 to Non Final Office Action dated Feb. 21, 2019", 9 pgs.
"U.S. Appl. No. 15/861,389, Non Final Office Action dated Nov. 29, 2018", 12 pgs.
"U.S. Appl. No. 15/861,389, Notice of Allowance dated May 22, 2019", 8 pgs.
"U.S. Appl. No. 15/861,389, Preliminary Amendment filed Jan. 3, 2018", 6 pgs.
"U.S. Appl. No. 15/861,389, Preliminary Amendment filed Jul. 2, 2018", 8 pgs.
"U.S. Appl. No. 15/861,389, Response filed Apr. 29, 2019 to Non Final Office Action dated Nov. 29, 2018", 15 pgs.
"U.S. Appl. No. 16/545,159, Notice of Allowance dated Nov. 16, 2020", 9 pgs.
"U.S. Appl. No. 16/545,159, Preliminary Amendment filed Dec. 2, 2019", 7 pgs.
"U.S. Appl. No. 16/545,159, Supplemental Notice of Allowability dated Dec. 31, 2020", 5 pgs.
"U.S. Appl. No. 16/703,328, Final Office Action dated Apr. 16, 2021", 26 pgs.
"U.S. Appl. No. 16/703,328, Non Final Office Action dated Nov. 25, 2020", 35 pgs.
"U.S. Appl. No. 16/703,328, Response filed Feb. 15, 2021 to Non Final Office Action dated Nov. 25, 2020", 13 pgs.
"Blood loss measurement: Technology opportunity assessment", Merck for Mother's Program, (2012), 9 pgs.
"Chinese Application Serial No. 201280033911.3, Office Action dated Feb. 4, 2017", with English translation of claims, 7 pgs.
"Chinese Application Serial No. 201280033911.3, Office Action dated Jul. 8, 2016", with English translation of claims, 10 pgs.
"Chinese Application Serial No. 201280033911.3, Office Action dated Nov. 4, 2015", with English translation of claims, 5 pgs.
"European Application Serial No. 12810640.8, Extended European Search Report dated Apr. 1, 2015", 8 pgs.
"European Application Serial No. 12810640.8, Intention to Grant dated Mar. 29, 16", 58 pgs.
"European Application Serial No. 12810640.8, Invitation pursuant to Rule 63(1) EPC dated Dec. 22, 2014", 3 pgs.
"European Application Serial No. 12810640.8, Response filed Feb. 20, 2015 to Invitation pursuant to Rule 63(1) EPC dated Dec. 22, 2014", 2 pgs.
"European Application Serial No. 12810640.8, Response filed Oct. 16, 2015 to Extended European Search Report dated Apr. 1, 2015", 10 pgs.
"European Application Serial No. 12810640.8, Response filed Oct. 22, 2014 to Communication pursuant to Rules 161(2) and 162 EPC dated May 16, 2014", 10 pgs.
"European Application Serial No. 13790449.6, Extended European Search Report dated Nov. 17, 2015", 7 pgs.
"European Application Serial No. 13790688.9, Extended European Search Report dated Nov. 23, 2015", 9 pgs.
"European Application Serial No. 15780653.0, Extended European Search Report dated Jul. 26, 2017", 12 pgs.
"European Application Serial No. 16183350.4, Communication Pursuant to Article 9 4(3) EPC dated Feb. 13, 2018", 6 pgs.
"European Application Serial No. 16183350.4, Extended European Search Report dated Nov. 4, 2016", 8 pgs.
"European Application Serial No. 16183350.4, Intention to Grant dated Jan. 4, 2019", 114 pgs.
"European Application Serial No. 16183350.4, Intention to Grant dated Jul. 24, 2018", 61 pgs.
"European Application Serial No. 16183350.4, Response filed Jun. 14, 2018 to Communication Pursuant to Article 94(3) EPC dated Feb. 13, 2018", 17 pgs.
"European Application Serial No. 16183350.4, Response filed Jun. 20, 2017 to Extended European Search Report dated Nov. 4, 2016", 5 pgs.
"European Application Serial No. 16880150.4, Extended European Search Report dated Jul. 9, 2019", 9 pgs.
"European Application Serial No. 19156549.8, Extended European Search Report dated Jul. 12, 2019", 8 pgs.
"European Application Serial No. 19156549.8, Response filed Apr. 28, 2020 to Extended European Search Report dated Jul. 12, 2019", 11 pgs.
"Indian Application Serial No. 754/DELNP/2014, Office Action dated Jan. 24, 2020", w/ English translation, 5 pgs.
"Indian Application Serial No. 754/DELNP/2014, Response filed Jul. 20, 2020 to Office Action dated Jan. 24, 2020", w/ English claims, 29 pgs.
"International Application Serial No. PCT/US2012/045969, International Preliminary Report on Patentability dated Apr. 10, 2014", 6 pgs.
"International Application Serial No. PCT/US2012/045969, International Search Report dated Sep. 17, 2012", 2 pgs.
"International Application Serial No. PCT/US2012/045969, Written Opinion dated Sep. 17, 2012", 4 pgs.
"International Application Serial No. PCT/US2013/021075, International Search Report dated Mar. 26, 2013", 2 pgs.
"International Application Serial No. PCT/US2013/021075, Written Opinion dated Mar. 26, 2013", 6 pgs.
"International Application Serial No. PCT/US2013/040976, International Search Report dated Sep. 24, 2013", 2 pgs.
"International Application Serial No. PCT/US2013/040976, Written Opinion dated Sep. 24, 2013", 4 pgs.
"International Application Serial No. PCT/US2015/026036, International Search Report dated Jul. 24, 2015", 2 pgs.
"International Application Serial No. PCT/US2015/026036, Written Opinion dated Jul. 24, 2015", 6 pgs.
"International Application Serial No. PCT/US2015/026041, International Preliminary Report on Patentability dated Oct. 27, 2016", 8 pgs.
"International Application Serial No. PCT/US2015/026041, International Search Report dated Jul. 24, 2015", 2 pgs.
"International Application Serial No. PCT/US2015/026041, Written Opinion dated Jul. 24, 2015", 6 pgs.
"International Application Serial No. PCT/US2016/068540, International Search Report dated Mar. 30, 2017", 3 pgs.
"International Application Serial No. PCT/US2016/068540, Written Opinion dated Mar. 30, 2017", 8 pgs.

(56) References Cited

OTHER PUBLICATIONS

"Japanese Application Serial No. 2014-519099, Notice of Reasons for Rejection dated Mar. 10, 2015", w/ English Translation, 5 pgs.

"Japanese Application Serial No. 2014-519099, Response filed Apr. 8, 2015 to Notice of Reasons for Rejection dated Mar. 10, 2015", 12 pgs.

"Optimizing protocols in obstetrics", ACOG, Series 2, (2012), 25 pgs.

"Quantification of blood loss: AWHONN practice brief No. 1", AWHONN Practice Brief, (2014), 1-3.

Adkins, A R, et al., "Accuracy of blood loss estimations among anesthesia providers", AANA Journal 82, (2014), 300-306.

Aklilu, A, "Gauss Surgical Measures Blood Loss with a Smartphone", [Online]. Retrieved from the Internet: <http://www.health2con.com/news/2012/06/14/gauss-surgical-measures-blood-loss-with-a-smartphone<, (Jun. 14, 2012).

Al-Kadri, H M, et al., "Effect of education and clinical assessment on the accuracy of postpartum blood loss estimation", BMC Preq. Childbirth 14, 110, 7 pgs.

Bellad, et al., "Standardized Visual Estimation of Blood Loss during Vaginal Delivery with its Correlation Hematocrit Changes—A Descriptive Study", South Asian Federation of Obstetrics and Gynecology 1.1, (2009), 29-34.

Bose, P, et al., "Improving the accuracy of estimated blood loss at obstetric haemorrhage using clinical reconstructions", BJOG 113(8), (2006), 919-924.

Eire, N, et al., "Perioperative blood loss assessment—How accurate?", Indian J. Anaesth. 50(1), (2006), 35-38.

Habak, P J, et al., "A comparison of visual estimate versus calculated estimate of blood loss at vaginal delivery", British J. Med. Medical Res. 11(4), (2016), 1-7.

Holmes, A A, et al., "Clinical evaluation of a novel system for monitoring surgical hemoglobin loss", Anesth. Analg. 119, (2014), 588-594.

Jones, R, "Quantitative measurement of blood loss during delivery", AWHONN, (2015), S41.

Kamiyoshihara, M, et al., "The Utility of an Autologous Blood Salvage System in Emergency Thoracotomy for a Hemothorax After Chest Trauma", Gen. Thorac. Cardiovasc. Surg. 56, (2008), 222.

Lyndon, A, et al., "Blood loss: Clinical techniques for ongoing quantitative measurement", CMQCC Obstetric Hemorrhage Toolkit, (2010), 1-7.

Lyndon, A, et al., "Cumulative quantitative assessment of blood loss", CMQCC Obstetric Hemorrhage Toolkit Version 2.0, (2015), 80-85.

Manikandan, D, et al., "Measurement of blood loss during adenotonsillectomy in children and factors affecting it", Case Reports in Clinical Medicine 4, (2015), 151-156.

Pogorelc, D, "iPads in the OR: New Mobile Platform to Monitor Blood Loss During Surgery", MedCityNews, [Online]. Retrieved from the Internet: <http://medcitynews.com/2012/06/ipads-in-the-or-new-mobile-platform-to-monitor-blood-loss-during-surgery>, (Jun. 6, 2012), 4 pgs.

Roston, R B, et al., "Chapter 9: Blood loss: Accuracy of visual estimation", A comprehensive textbook of postpartum hemorrhage: An essential clinical reference for effective management 2nd edition, Sapiens, (2012), 71-72.

Sant, et al., "Exsanguinated Blood Volume Estimation Using Fractal Analysis of Digital Images", Journal of Forensic Sciences 57, (2012), 610-617.

Satish, et al., "U.S. Appl. No. 15/594,017, filed May 12, 2017", 65 pgs.

Satish, et al., "U.S. Appl. No. 16/392,345, filed Apr. 23, 2019", 40 pgs.

Satish, et al., "U.S. Appl. No. 15/416,986, filed Jan. 26, 2017", 41 pgs.

Satish, et al., "U.S. Appl. No. 15/390,017, filed Dec. 23, 2016", 34 pgs.

Satish, S, et al., "System and Methods for Managing Blood Loss of a Patient", U.S. Appl. No. 15/943,561, filed Apr. 2, 2018, 66 pgs.

Schorn, M N, et al., "Measurement of blood loss: Review of the literature", J. Midwifery and Women's Health 55, (2010), 20-27.

Sukprasert, M, et al., "Increase accuracy of visual estimation of blood loss from education programme", J. Med. Assoc. Thai 89, (2006), S54-S59.

U.S. Appl. No. 13/544,679/U.S. Pat. No. 8,897,523, filed Jul. 9, 2012, System and Method for Counting Surgical Sponges.

U.S. Appl. No. 13/544,646/U.S. Pat. No. 8,792,693, filed Jul. 9, 2012, System and Method for Estimating Extracorporeal Blood Volume in a Physical Sample.

U.S. Appl. No. 13/544,664/U.S. Pat. No. 9,652,655, filed Jul. 9, 2012, System and Method for Estimating Extracorporeal Blood Volume in a Physical Sample.

U.S. Appl. No. 15/594,017/U.S. Pat. No. 10,528,782, filed May 12, 2017, System and Method for Estimating Extracorporeal Blood Volume in a Physical Sample.

U.S. Appl. No. 16/703,328, filed Dec. 4, 2019, System and Method for Estimating Extracorporeal Blood Volume in a Physical Sample.

U.S. Appl. No. 15/861,389/U.S. Pat. No. 10,426,356, filed Jan. 3, 2018, Method for Estimating a Quantity of a Blood Component in a Fluid Receiver and Corresponding Error.

U.S. Appl. No. 14/687,860/U.S. Pat. No. 9,870,625, filed Apr. 15, 2015, Method for Estimating a Quantity of a Blood Component in a Fluid Receiver and Corresponding Error.

U.S. Appl. No. 16/545,159/U.S. Pat. No. 10,957,179, filed Aug. 20, 2019, Method for Estimating a Quantity of a Blood Component in a Fluid Receiver and Corresponding Error.

"U.S. Appl. No. 16/703,328, Examiner Interview Summary dated Sep. 10, 2021", 1 pg.

"U.S. Appl. No. 16/703,328, Notice of Allowance dated Sep. 3, 2021", 12 pgs.

\* cited by examiner

METHOD FOR ESTIMATING A QUANTITY OF A BLOOD COMPONENT IN A FLUID RECEIVER AND CORRESPONDING ERROR

CROSS-REFERENCE TO RELATED APPLICATIONS

CROSS-REFERENCE TO RELATED APPLICATIONS

This application is a continuation of U.S. patent application No. 16/545,159, filed on 20 Aug. 2019, now U.S. Pat. No. 10,957,179, which is a continuation of U.S. patent application No. 15/861,389, filed on 03 Jan. 2018, now U.S. Pat. No. 10,426,356, which is a divisional of U.S. patent application No. 14/687,860, filed on 15 Apr. 2015, now U.S. Pat. No. 9,870,625, which is a continuation-in-part of U.S. patent application No. 13/544,646, filed on 09 Jul. 2012, now U.S. Pat. No. 8,792,693, which claims the benefit of U.S. Provisional Patent Application No. 61/506,082, filed on 09 Jul. 2011, U.S. Provisional Patent Application No. 61/646,818, filed on 14 May 2012, and U.S. Provisional Patent Application No. 61/646,814, filed on 14 May 2012, all of which are herein incorporated in their entireties by this reference. U.S. patent application No. 14/687,860, filed on 15 Apr. 2015 also claims the benefit of U.S. Provisional Patent Application No. 61/980,026, filed on 15 Apr. 2014, which is incorporated herein in its entirety by this reference.

TECHNICAL FIELD

This invention relates generally to the surgical field, and more specifically to a new and useful method for communicating estimated blood loss parameters of a patient to a user for use in surgical practice.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Method and Applications

Figure 1A:
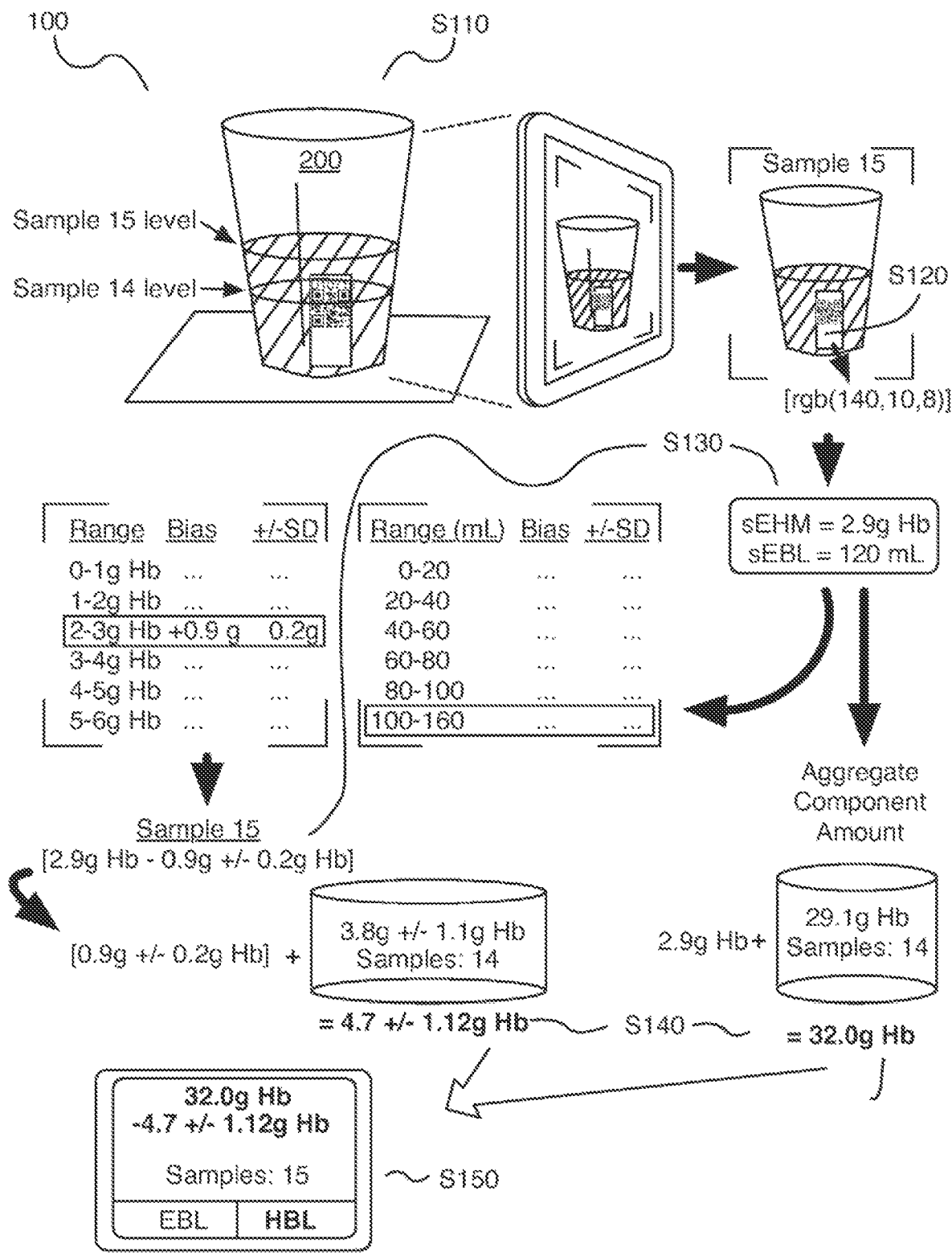
FIGS. 1A, 1B, and 1C are flowchart representations of different embodiments of a method for communicating estimated blood loss parameters of a patient to a user.
Figure 1B:
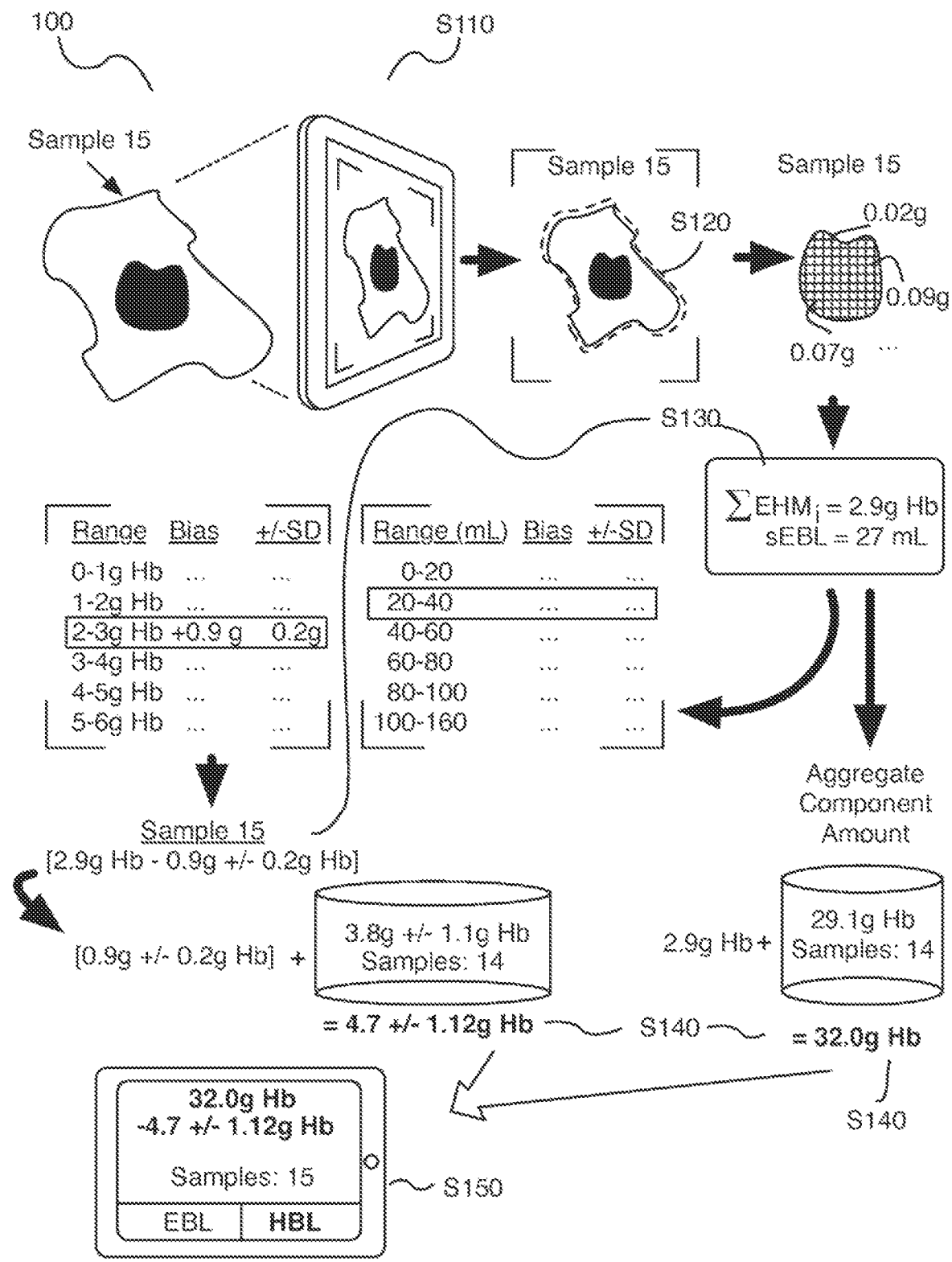
Figure 1C:
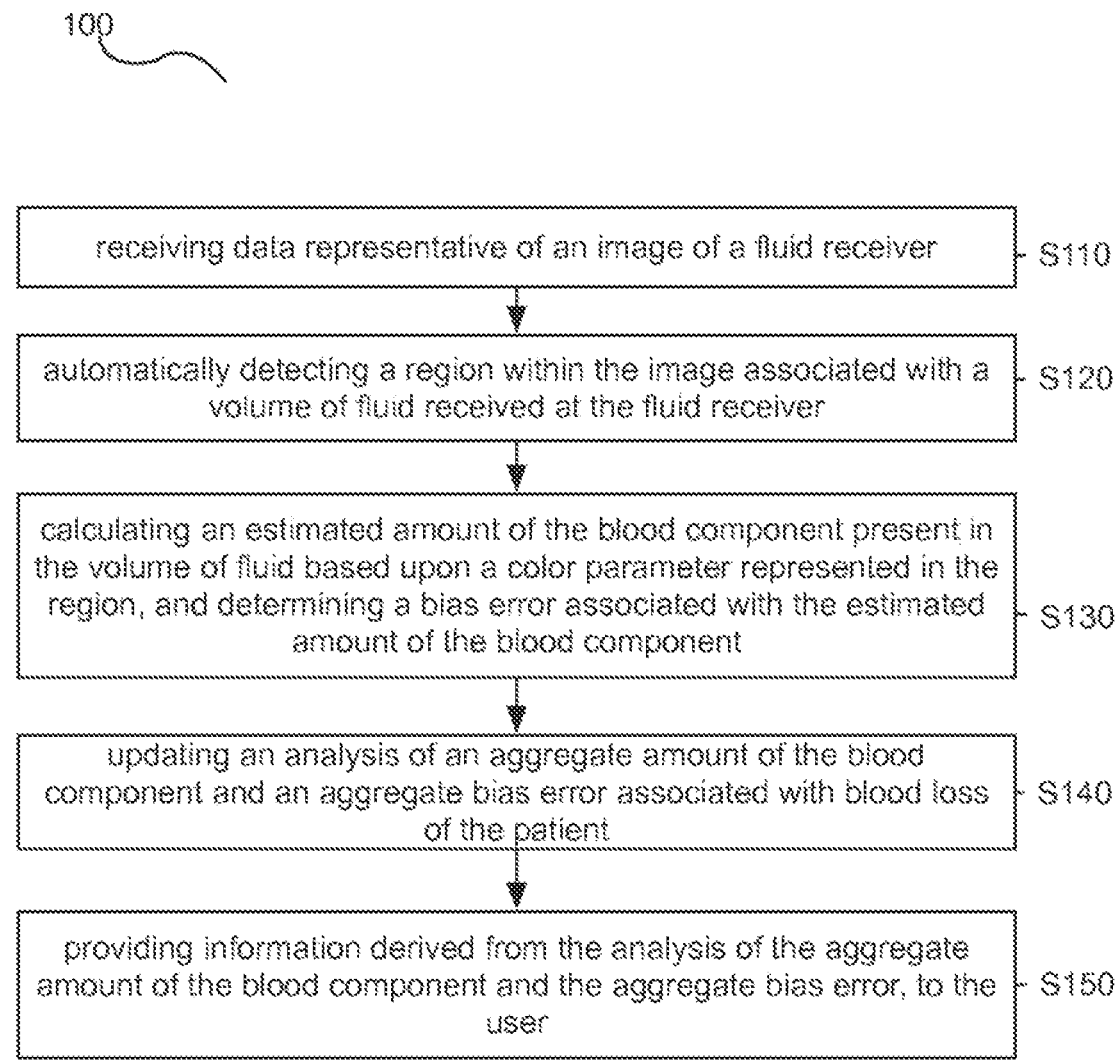

As shown in FIGS. 1A, 1B, and 1C, a method 100 for communicating estimated blood loss parameters of a patient to a user comprises: receiving data representative of an image of a fluid receiver S110; automatically detecting a region within the image associated with a volume of fluid received at the fluid receiver S120; calculating an estimated amount of the blood component present in the volume of fluid, and determining a bias error associated with the estimated amount of the blood component S130; updating an analysis of an aggregate amount of the blood component and an aggregate bias error associated with blood loss of the patient S140; and providing information derived from the analysis of the aggregate amount of the blood component and the aggregate bias error, to the user S150.

Figure 2A:
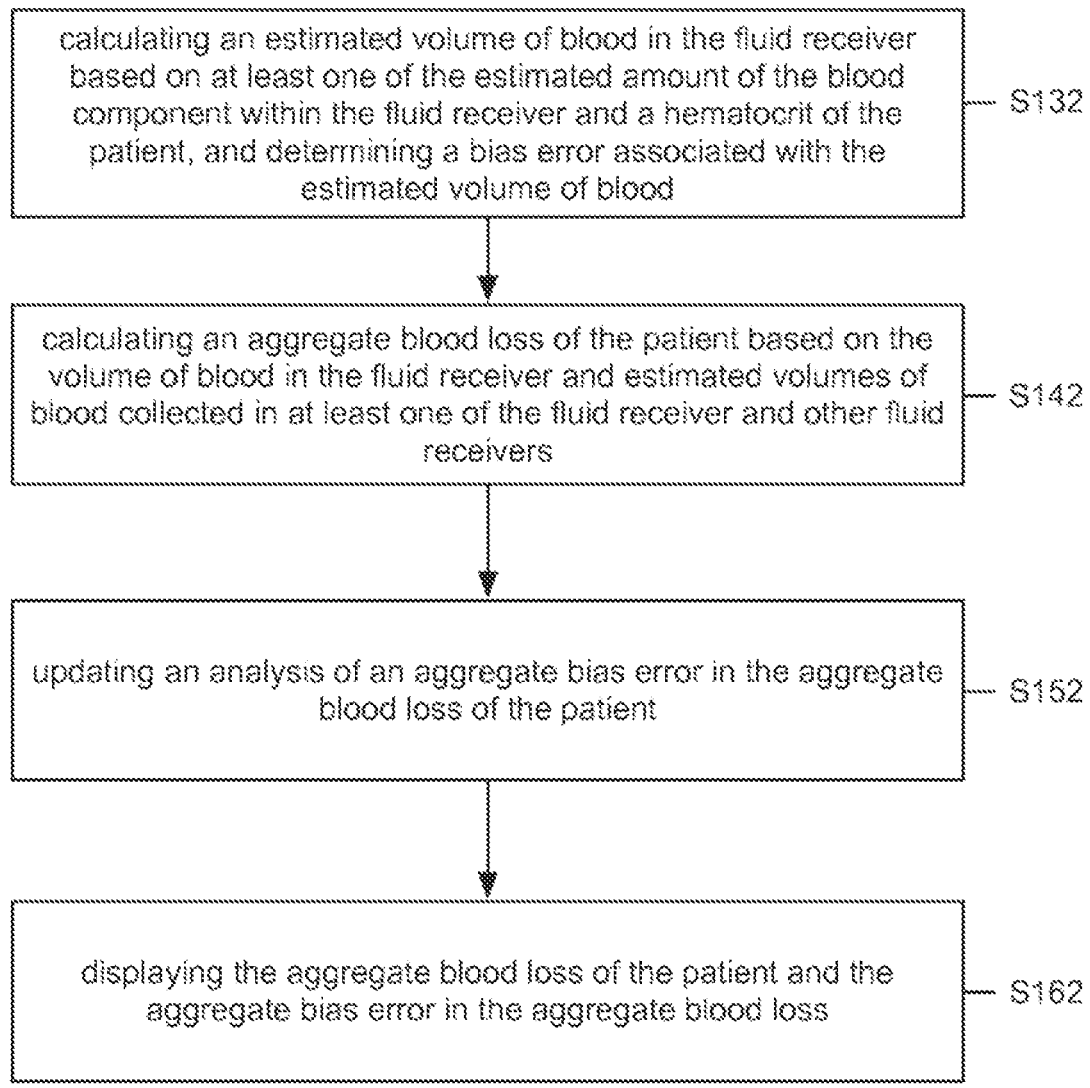
FIG. 2A is a flowchart representation of one variation of the method for communicating estimated blood loss parameters of a patient to a user.
Figure 2B:
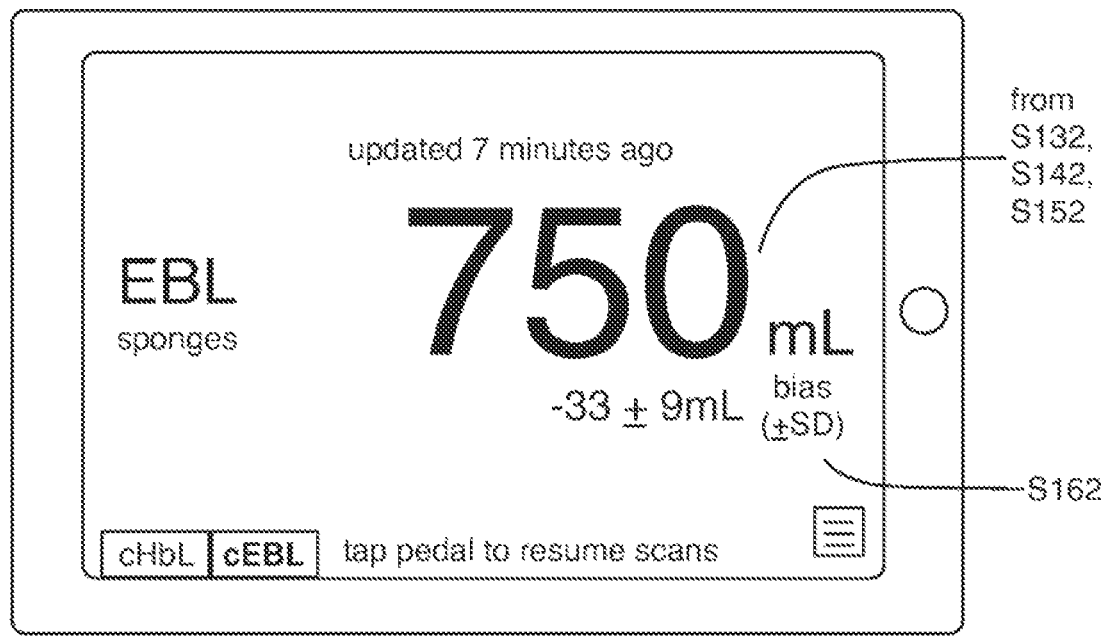
FIG. 2B is a graphical representation of one variation of the method for communicating estimated blood loss parameters of a patient to a user.

As shown in FIGS. 2A and 2B, the method 100 can further include: calculating an estimated volume of blood in the fluid receiver based on at least one of the estimated amount of the blood component within the fluid receiver and a hematocrit of the patient, and determining a bias error associated with the estimated volume of blood S132; calculating an aggregate blood loss of the patient based on the volume of blood in the fluid receiver and estimated volumes of blood collected in at least one of the fluid receiver and other fluid receivers S142; updating an analysis of an aggregate bias error in the aggregate blood loss of the patient S152; and displaying the aggregate blood loss of the patient and the aggregate bias error in the aggregate blood loss S162.

Generally, the method 100 functions to implement machine vision to estimate the amount of hemoglobin (e.g., intracellular hemoglobin, free hemoglobin, hemoglobin derivatives, etc.), whole blood, platelet plasma, white blood cells, or other blood component contained in one or more fluid receivers, such as a surgical textile (e.g., surgical gauze, sponge, a surgical dressing, a surgical towel, an absorbent pad, a test strip, a drape, etc.) or a canister (e.g., suction canister, blood salvage canister, fluid receiving bag, a cell salvage system, a drain device, etc.). In particular, the method 100 analyzes data derived from a (digital) photographic image of a fluid receiver (i.e., a "sample") to identify a region of the sample in the image, to estimate an amount (e.g., a mass, a weight) of a blood component in the sample based upon a color parameter represented in the sample, to estimate and/or derive error-related metrics (e.g, bias, standard deviation, Bland-Altman limits-of-agreement, confidence intervals around these and other metrics, etc.) in the estimated amount of the blood component in the sample, and to visually present the estimated amount of the blood component and the associated estimated bias error to a user (e.g., a nurse, anesthesiologist, etc.) through a digital display or other digital user interface. The method 100 can similarly function to estimate amounts of non-blood components (e.g., saline, ascites, bile, irrigant saliva, gastric fluid, mucus, pleural fluid, fecal matter, urine, etc.) and associated errors (e.g., single-sample errors, aggregate errors, etc.), and to present this information to the user. The method 100 can also calculate aggregate amounts of blood components and/or non-blood components, determine corresponding aggregate bias errors, and then provide information indicative of these aggregate values to the user, such as, for example, to assist the user in tracking patient volemic status over time.

Therefore, rather than presenting a single value of estimated hemoglobin mass or aggregate blood volume in one or a series of fluid receivers, the method 100 can augment such values with corresponding estimated error values, thereby enabling a user (e.g., a nurse, an anesthesiologist, a pediatrician, etc.) to better understand limitations of the hemoglobin mass and blood volume estimates in real-time in a clinical setting. The method 100 can thus calculate aggregate error values throughout a surgical operation or other clinical setting and present the additional error data to the user to enable the user to formulate a more complete clinical picture of the patient, thereby enabling the user to make a more informed decision of patient needs. For example, a user may handle or implement hemoglobin mass and aggregate blood volume estimates—output through the method—differently for different types of patients (e.g., children, adults, and geriatrics, etc.) based on error estimates calculated and presented to the user through the method.

The method 100 can therefore implement/augment methods and techniques described in U.S. application Ser. No. 13/544,646 entitled "System and Method for Estimating Extracorporeal Blood Volume in a Physical Sample" and filed on 9 Jul. 2012, U.S. application Ser. No. 13/894,054 entitled "System and Methods for Managing Blood Loss of a Patient" and filed on 14 May 2013, U.S. application Ser. No. 13/738,919 entitled "System and Method for Estimating a Quantity of a Blood Component in a Fluid Canister" and filed on 10 Jan. 2013, and U.S. application Ser. No. 14/072,625 entitled "Method for Triggering Blood Salvage" and filed on 5 Nov. 2013, which are each incorporated herein in its entirety by this reference.

The method 100 can be useful in estimating an amount of a blood component such as whole blood, red blood cells, hemoglobin, platelets, plasma, white blood cells, or other blood component or combination of blood components absorbed into a fluid receiver through non-contact means and in real-time, such as during a surgery or other medical event. A patient's blood loss and euvolemia status can thus be tracked according to the data, such as described in U.S. patent application Ser. No. 14/072,625. However, the method 100 can be applicable in any other scenario or environment to estimate an amount of blood and/or a blood component in a fluid receiver. For example, the method can similarly analyze an image of an article of clothing, a ground, table, wall, or floor surface, an external skin surface, a surgical glove, a surgical implement, or any other surface, material, substrate, or object to estimate an amount of blood component or non-blood component of a patient or other individual. Further, the method can estimate blood component metrics such as mass, volume, concentration, viscosity, and/or other suitable metric. Additionally or alternatively, the method 100 can be useful in estimating an amount of a non-blood component such as saline, ascites, bile, irrigant saliva, gastric fluid, mucus, pleural fluid, fecal matter, urine, or other bodily fluid through non-contact means and in real-time. Patient data relating to each tracked bodily fluid can thus be charted and/or analyzed.

The method 100 can thus be implemented by a computing system that functions as a fluid receiver analyzer in analyzing a photographic image of a fluid receiver to estimate the quantity and/or quality of a fluid (or fluid component) contained therein. The computing system can include modules in one or more of: a cloud-based system (e.g., Amazon EC2), a mainframe computer system, a grid-computer system, and any other suitable computer system. For example, the method can be implemented by a handheld (e.g., mobile) computing device, such as a smartphone, a digital music player, or a tablet computer executing a native blood component analysis application as shown in FIGS. 1A and 1B. For example, an image acquisition device integral within or detached from the computing device can capture an image of a fluid receiver, and a processor integrated into or detached from the computing device can implement blocks of the method 100 to extrapolate from the image the amount of blood component and corresponding bias error with respect to the fluid receiver. The computing system can additionally or alternatively communicate with a remote server, such as over the Internet via wireless or other radio-frequency connection, the server can perform one or more Blocks of the method, and one or more outputs of the method can be transmitted from the remote server back to the computing device for further analysis and/or subsequent presentation to a user. Alternatively, one or more outputs of the method 100 can be calculated by the computing device and transmitted to the remote server for future reference. The computing device can also include or can be coupled to a digital display, and the method 100 can present information to the user through the display.

Preferably, when performing one or more Blocks of the method 100, the computing device maintains connectivity with the remote server. Alternatively, the computing device can be disconnected from the remote server for some or all of the Blocks of the method. If the computing device loses connectivity with the server while performing the Blocks of the method, any network communications are preferably saved and resubmitted when connectivity is reestablished, enabling the continuation of the Blocks of the method 100.

The fluid receiver analyzer can further communicate (e.g., via Bluetooth) with another one or more systems implementing any of the methods described in U.S. application Ser. Nos. 13/544,646, 13/894,054, 13/738,919, and/or 14/072,625 to form a fluid management system for generating a substantially comprehensive estimate of one or more blood components (e.g., extracorporeal blood volume, aggregate patient blood loss), non-blood components, and/or biological statuses (e.g., patient euvolemia status) based on patient fluids collected in fluid receivers. However, the method 100 can be implemented in or by any other computing system, computing device, or combination thereof. Furthermore, variations of the method 100 can be adapted to process any other set of measurements (e.g., discrete measurements taken at a set of time points, measurements from video data, etc.), to determine an error associated with each of the set of measurements, to aggregate the measurements and the errors associated with the measurements, and to provide information derived from the aggregated measurements and aggregate errors to a suitable entity in order to enhance a subsequent analysis or response to the set of measurements.

2. Estimated Amount of Blood Component

Block S110 recites: receiving data representative of an image of a fluid receiver, Block S120 recites automatically detecting a region within the image associated with a volume of fluid received at the fluid receiver, and Block S130 recites calculating an estimated amount of the blood component present in the volume of fluid based upon a color parameter represented in one or more regions, and determining an associated bias error. Blocks S110, S120, and S130 can be implemented as described in U.S. application Ser. Nos. 13/544,646, 13/894,054, 13/738,919, 14/072,625, and/or 14/687,842, which is incorporated herein in its entirety by this reference.

In some variations, Block S140 can include, in part: estimating an aggregate amount of the blood component associated with blood loss of the patient. In one variation, Block S140 of the method can include estimating an aggregate hemoglobin loss of a patient based upon the mass of hemoglobin in the fluid receiver and estimated masses of hemoglobin aggregated from at least one of the fluid receiver and a set of other fluid receivers. Thus, once Block S130 in this variation estimates an amount of hemoglobin in a single fluid receiver—shown in a current photographic image—Block S140 can sum this estimated amount with a running tally of hemoglobin amounts derived from fluid received into the fluid receiver and/or fluid received into other fluid receivers captured and analyzed in image data, thereby maintaining a total (i.e., aggregate) estimate of the patient's hemoglobin loss (or a aggregate amount of patient hemoglobin collected in one or more fluid receivers). Block S140 can then pass this data to Block S150 for presentation to a user.

Figure 6:
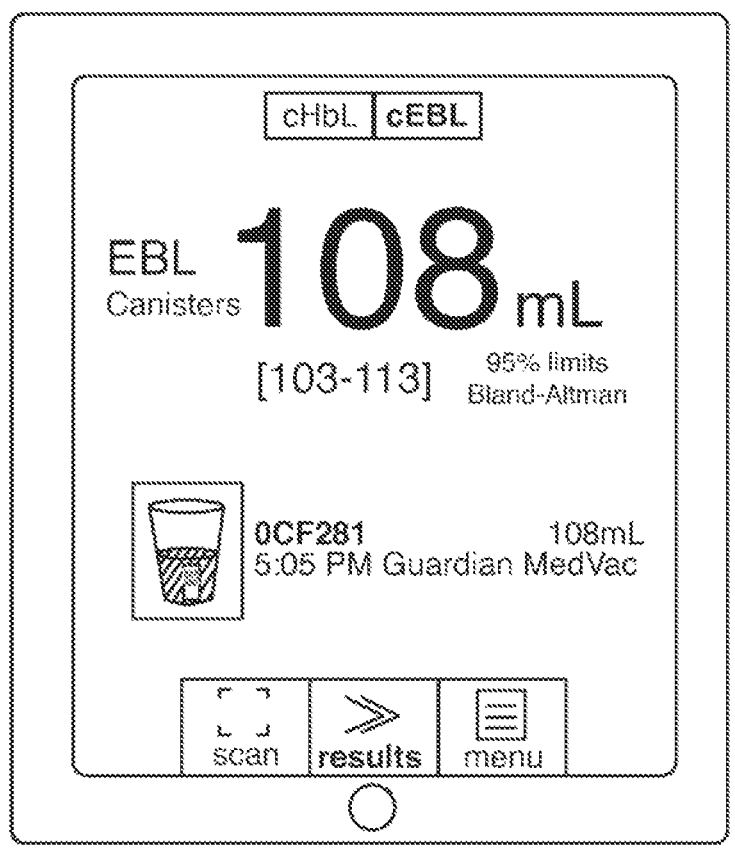
FIG. 6 is a graphical representation of one variation of the method for communicating estimated blood loss parameters of a patient to a user.

As shown in FIGS. 2A, 2B, and 6, another variation of the method 100 can include Block S132, which recites, in part: estimating a volume of blood in the fluid receiver based on the mass of hemoglobin in the fluid receiver and an estimated hematocrit of the patient. Preferably, the hematocrit is a known value that is manually entered by the user (e.g., a nurse, an anesthesiologist, etc.). The hematocrit can be determined through traditional calculations or approaches such as microhematocrit centrifugation. Alternatively, the hematocrit can be automatically determined (e.g., algorithmically, automatically retrieved from an electronic health record, etc.) and entered into the computing system by performing Blocks of the method 100 on one or more volume of fluids received by one or more fluid receivers.

In variations of the method 100 including Block S132, the method 100 can further include Block S142, which recites: estimating an aggregate blood loss of the patient based on the volume of blood in the fluid receiver and estimated volumes of blood in the fluid receiver and/or other fluid receivers, can similarly sum estimated blood volumes derived from the fluid receiver(s) to estimate an aggregate patient blood loss (or an aggregate amount of patient blood collected in one or more fluid receivers) and then pass these data to Block S162 for presentation to the user.

Alternatively, in one workflow including Blocks S120, S140, S142, and S152: Block S120 can implement machine vision techniques to identify a particular type of the fluid receiver in the photographic image, and Block S140 can group the current fluid receiver with fluid receivers of the same or similar type (e.g., in relation to manufacturer and model, material, and/or size, etc.). Block S140 can then sum estimated hemoglobin quantities for all fluid receivers of the same or similar type, material, size, etc. and determine error estimation on a per-fluid receiver-type basis for these aggregate hemoglobin quantity values. Block S142 can similarly sum estimated aggregate blood quantities for all fluid receivers of the same or similar type, material, size, etc. and pass these aggregate blood volume values to Block S152 for error estimation on a per-fluid receiver-type basis.

Block S140 and Block S142 can also enable determination of the aggregate hemoglobin content and aggregate blood volume in the fluid receiver(s) for providing a (more) complete view of the patient's blood loss and euvolemia status, as described in U.S. patent application Ser. No. 14/072,625.

Generally, Blocks S110, S120, S130, S132, S140, and/or S142 also implement methods or techniques described in U.S. patent application Ser. Nos. 13/544,646, 14/072,625, and/or 13/738,919. However, Blocks S110, S120, S130, S132, S140, and/or S142 can implement any other method or technique to estimate the amount of any blood component (e.g., surgical gauze, sponge, a surgical dressing, a surgical towel, an absorbent pad, a test strip, a drape, etc.) or non-blood component (e.g., saline, ascites, bile, irrigant saliva, gastric fluid, mucus, pleural fluid, urine, fecal matter) in a particular fluid receiver or other sample. Variations of Block S140, in relation to updating an analysis of an aggregate bias error corresponding to an aggregate estimated amount of the blood component, are further described in Section 3 below:

3. Estimated Error

Block S140 recites, in part: updating an analysis of an aggregate bias error corresponding to an aggregate estimated amount of the blood component, and Block S152 of the method recites updating an analysis of an aggregate bias error in the aggregate blood loss ("cEBL") of the patient. In variations, Block S140 functions to estimate an aggregate bias error corresponding to the aggregate estimated hemoglobin mass in one or more fluid receivers ("cEHM"). In particular, Block S130 estimates a bias error for the estimated hemoglobin mass associated with each image of the fluid receiver(s) and Block S140 sums these bias errors as each additional image of the fluid receiver(s) is imaged and analyzed. As shown in FIGS. 2A and 2B, Block S152 similarly functions to estimate an aggregate bias error based on individual bias errors for the estimated amounts of blood loss with respect to the individual volumes of fluids associated with one or more fluid receivers.

In one implementation, Block S140 calculates a bias and a standard deviation of aggregate error ("SD(error)"), which may indicate a precision of the estimate of the aggregate bias error based on an out-of-sample study population. For example, Block S130 can estimate hemoglobin masses of 2 g, 6 g, 4 g, 1 g, 5 g, and 6 g, as well as biases of 0.2 g, 1 g, 0.05 g, 0.5 g, 0.7 g, and 1 g for a sequence of six surgical gauze sponges. Block S140 can then estimate an aggregate hemoglobin mass of 24 g, an aggregate bias of +3.45 g, and a standard deviation of aggregate bias of 2.5 g. Block S140 can thus output an aggregate estimated error of +95 g to +5.95 g, and, in this example, Block S150 can present to the user an aggregate estimated hemoglobin mass of 24 g+0.95 g to +5-95 g, thus indicating that the "true" aggregate hemoglobin volume in the six surgical gauze sponges falls between 24.95 g and 29.95 g.

In another implementation, Block S140 calculates a bias and a standard deviation of aggregate error ("SD(error)"), which may indicate a precision of the estimate of the aggregate bias error based on an out-of-sample study population. For example, Block S130 can estimate hemoglobin masses of 2 g, 6 g, 4 g, 1 g, 5 g, and 6 g, as well as biases of 0.2 g, 1 g, 0.05, 0.5 g, 0.7 g, and 1 g for a sequence of images taken of a canister as the canister receiving fluid from the patient. Block S140 can then estimate an aggregate hemoglobin mass of 24 g, an aggregate bias of +3.45 g, and a standard deviation of aggregate bias of 2-5 g. Block S140 can thus output an aggregate estimated error of +0.95 g to +5.95 g, and, in this example, Block S150 can present to the user an aggregate estimated hemoglobin mass of 24 g+0.95 g to +5-95 g, thus indicating that the "true" aggregate hemoglobin volume derived from fluid filling the canister falls between 24.95 g and 29.95 g.

3.1 Per-Sample Bias and Standard Deviation Test Data

As shown in FIGS. 1A and 1B, variations of the method 100 for determining the bias error comprise generating a comparison between the estimated amount of a blood component and a set of ranges for amounts of the blood component, where the set of ranges for amounts of the blood component is determined from a set of fluid samples having a set of both (a) known amounts of the blood component paired with (b) estimated amounts of the blood component derived from image analysis of each of the set of fluid samples within a version of the fluid receiver. A range from the set of ranges is selected based upon the comparison, and the bias error and standard deviation in the bias error associated with the range is retrieved.

In one implementation, a per-sample bias (+/−SD) specific to a range of possible estimated amounts of blood component (e.g., estimated amounts of hemoglobin mass) is computed from (empirical) verification and validation data for each type of fluid receiver. For example, for each fluid receiver type approved for imaging and analysis with the method, a test set of (at least) fifty samples associated with fluid receivers of the same size, material, manufacturer, and/or model can be tested to calculate a per-sample bias specific to this type of fluid receiver (e.g., canister, surgical gauze sponge, absorbent pad, surgical textile, test strip, fluid receiving bag, drain system, cell salvage system, etc.). Alternatively, rather than associating per-sample biases (+/−SD) with ranges of values, the per-sample biases (+/−SD) can be specific to discrete values of amounts of blood component. As such, direct comparison to the discrete values and/or interpolation between the discrete values can be used in blocks of the method 100. Although specific mappings of keys (e.g., ranges or discrete values of amounts of blood component) to values (e.g., bias error (+/−SD)) have been discussed, any suitable type of key or value can be used for assigning a bias error (+/−SD) to an estimated amount of blood or non-blood component.

In this implementation, the per-sample bias for a particular type of fluid receiver can be calculated by creating a validation set of samples, each sample in the set containing a known (i.e., assayed) amount of the blood component (e.g., between 0 g and 6 g of hemoglobin). Each sample can then be imaged and analyzed—as in Blocks S110, S120, and S130—to generate corresponding image-based estimates of the amount of the blood component present in each sample. In one example, estimated amounts of hemoglobin mass are calculated for each sample (e.g., sEHM values), the samples are then rank-ordered (i.e., sorted) by their sEHM values in ascending order, and this sorted dataset is then split into the multiple sEHM subgroups, such as [sEHM≤1], [1<sEHM≤2], [2<sEHM≤3], [3<sEHM≤4], [4<sEHM≤5], and [sEHM>5]. A bias (+/−SD) of each subgroup is computed by comparing known hemoglobin mass against sEHM values for each sample in a particular subgroup, and calculating an arithmetic mean of the differences (i.e., sEHM—known hemoglobin mass) for each sample within the particular subgroup. Finally, a standard deviation ("SD") of the differences between biases of samples in a particular subgroup are calculated (e.g., according to a standard "n−1" method for computing standard deviation), and these standard deviations can be paired with a corresponding bias error for each subgroup in a lookup table (or other suitable format) specific to the fluid receiver type, such as shown in FIGS. 1A and 1B. The lookup table can thus be stratified into discrete (e.g., one-gram (1.0 g)) intervals of predicted sEHM to provide an out-of-sample estimate of bias error (+/−SD) for fluid receivers with sEHM values falling within a particular interval. However, any suitable sample size, rank-ordering criteria, subgroup step size, standard deviation method, etc. can be implemented to calculate a bias and/or a standard deviation for subgroups of samples where the amount of blood component is known and has been estimated through the Blocks of the method 100.

In other variations, lookup tables can be generated for fluid receiver types based on verification and validation data (or any other suitable type of data), for any other suitable type of blood component (e.g., whole blood, red blood cells, platelets, plasma, white blood cells, etc.) or non-blood component (e.g., saline, ascites, bile, irrigant saliva, gastric fluid, mucus, pleural fluid, urine, fecal matter, etc.). Depending upon the type of blood component or non-blood component analyzed, the method 100 can include accessing the lookup table corresponding to the specific component type. For example, three sets of lookup tables can be stored in the same database, where each set corresponds to one of three different types of blood components and where each set comprises lookup tables for approved (e.g., pre-analyzed) fluid receiver types. The method 100 can preferably access multiple lookup tables simultaneously to provide estimates of prediction bias (+/−SD) for different estimated amounts of blood components. In an implementation, three fluid receivers of different types (e.g., a sponge, a suction canister, and a towel) are identified in one or more images. Estimated amounts of both platelet content and hemoglobin mass are calculated for each of the volumes of fluid in the three fluid receivers, resulting in six estimated amounts of blood components (i.e., three platelet content amounts and three hemoglobin masses). The method 100 can subsequently identify the six lookup tables that are specific to the six possible combinations of fluid receiver type and blood component type (e.g., hemoglobin mass for sponge, platelet content for sponge, hemoglobin mass for suction canister, platelet content for suction canister, etc.). Estimates of prediction bias (+/−SD) can then be given for each of the six estimated amounts of blood component.

Bias and standard deviation values can thus be calculated for a particular type of fluid receiver and/or blood component for storage in a lookup table (or other suitable format). Blocks S130, S132, S140, and S152 can recall one or more lookup tables specific to one or more types of fluid receivers identified in a current image (e.g., identified through object recognition, object detection, etc.). In particular, Blocks S130, S132, S140, and S152 can apply data contained in the selected lookup table(s) to the estimated amount of blood component in a current sample to assign a bias and a standard deviation applicable to the current sample.

Similar methods can be implemented to calculate bias (and +/−SD) in whole blood volume estimates, such as through using a single validation set of samples assayed with blood of a static hematocrit value or through using a series of training sets of samples assayed with blood of different hematocrit values.

Such lookup tables can also be generated for different patient population types, such as pediatric patients, adult patients, geriatric patients, anemic patients, patients with histories of stroke, diabetic patients, and any other suitable population type, and Blocks S130, S132, S140, and S152 can select particular error models or lookup tables according to a characteristic or characterization of a current patient. Other patient characteristics can include, for example, medical history, genetics, gender, weight, age, height, race, health status, and/or diet. In an illustration, an amount of a blood component is estimated for a female with a history of high blood pressure, and a lookup table specific to females with high blood pressure is used to provide the bias (+/−SD) for the estimated amount of blood component. In other variations, lookup tables can be generated for different medical procedure characteristics (e.g., type of surgery, location of blood loss, localization of blood loss, etc.). Generally, lookup tables can be generated and tailored to any combination or number of fluid receiver types, blood component types, patient characteristics, medical procedure characteristics, and/or other suitable types of information.

The lookup table can be stored, for example, in a database (e.g., hierarchical, network, relational, object-oriented, etc.) accessible through a database management system. The database can be located on the computer system, the remote server, or any other suitable platforms for holding databases. Alternatively, the lookup table can be stored directly in the memory of the computer system, the remote server, or any other suitable platform with memory.

Alternatively, other approaches of providing a bias error for an estimated amount of blood or non-blood component can be used (e.g., template matching, a parametric model, machine learning, implementation of bias errors associated with system elements used in the method 100, etc.). Such approaches can use information regarding any combination or number of fluid receiver types, blood component types, patient characteristics, medical procedure characteristics, and/or other suitable types of information.

Additionally or alternatively, while bias error and standard deviation (e.g., in bias error) are determined in Blocks of the method 100 described herein, variations of the method 100 can be adapted to determine any other suitable statistics based upon a measurement and an aggregation of measurements including one or more of: limits-of-agreement (e.g., Bland-Altman limits-of-agreement), confidence intervals, coefficients of determination (e.g., $R^2$), root mean square errors, sum of square errors, sum of absolute errors, metrics derived from an error histogram (e.g., an aggregation of parameters derived from an error histogram using a Monte Carlo simulation), an interquartile range in an error metric, a minimum error value, a maximum error value, a mean error value, a median error value, and any other suitable type of statistic indicative of measurement/estimate quality. As such, in one example, an error histogram can be determined for each of a set of measurements (e.g., derived from each of a set of sponges, derived from each of a set of measurements associated with a fluid receiver, etc.), and a Monte Carlo simulation can be used to compute a histogram of the aggregate error, based upon the error histograms from each of the set of measurements. The method 100 can, however, implement any other suitable statistical component indicative of error, in providing information associated with a medical parameter, to a user.

3.2 Estimated Error: Hemoglobin Mass—Surgical Textile

In one implementation, Block S140 calculates an aggregate cEHM bias ($\Delta_T^{cEHM}$) by summing estimated per-surgical textile biases of all surgical textiles (e.g., surgical gauze, sponge, a surgical dressing, a surgical towel, an absorbent pad, a test strip, a drape, etc.) imaged and analyzed up to a current point as:

$$\Delta_T^{cEHM} = \sum_{i=1}^{n} \Delta_i^{cEHM},$$

wherein $\Delta_i^{cEHM}$ is the estimated cEHM bias of an individual surgical textile i, such as specific to the surgical textile type and to a range of EHM values of the surgical textile i.

Block S150 can then calculate an aggregate cEHM standard deviation of error (SEHM) by summing estimated per-surgical textile SD(error) of all surgical textile images and analyzed up to the current point as:

$$S_T^{cEHM} = \sqrt{\sum_{i=1}^{n} (S_i^{cEHM})^2},$$

wherein $S_i^{cEHM}$ is the estimated cEHM standard deviation of error of the surgical textile i, such as specific to the surgical textile type and to a range of EHM values corresponding to the surgical textile i.

Block S130 can thus implement the lookup table described above to assign specific cEHM bias ($\Delta_i^{cEHM}$) and cEHM standard deviation of error ($S_i^{cEHM}$) values to each new surgical textile imaged and analyzed in Blocks S110 and S120, outputs of which can be used to update the analysis in Block S140.

3.3 Estimated Error: Whole Blood Volume—Surgical Textile

Block S152 can similarly estimate an aggregate cEBL bias error ($\Delta_T^{cEBL}$) of all surgical textiles (e.g., surgical gauze, sponge, a surgical dressing, a surgical towel, an absorbent pad, a test strip, a drape, etc.) imaged and analyzed up to a current point as:

$$\Delta_T^{cEBL} = \sum_{i=1}^{n} \frac{\Delta_i^{cEHM}}{Hb_i},$$

wherein $\Delta_i^{cEHM}$ is the cEHM bias of a surgical textile i, such as specific to the surgical textile type and to a range of EHM values for the surgical textile i, and wherein $Hb_i$ is the user-entered estimate of the patient's laboratory derived hemoglobin (Hb) concentration (e.g., in g/ml or g/dl) corresponding to the time at which surgical textile i was used, as described in U.S. patent application Ser. No. 14/072,625. Additionally or alternatively, $Hb_i$ can be determined in any other suitable manner (e.g., using machine vision, using template matching, using a parametric model, etc.) as described in U.S. patent application Ser. No. 14/072,625.

Block S152 can further calculate an estimated aggregate cEBL standard deviation of error ($S_T^{cEBL}$) as:

$$S_T^{cEBL} = \sqrt{\sum_{i=1}^{n} \left(\frac{S_i^{cEHM}}{Hb_i}\right)^2},$$

wherein $S_i^{cEHM}$ is a standard deviation of a surgical textile i, such as specific to the type of surgical textile and the predicted cEHM of the surgical textile i. and wherein $Hb_i$ is the user-entered estimate of the patient's laboratory-derived Hb concentration corresponding to the time at which surgical textile i was used (or imaged). Additionally or alternatively, $Hb_i$ can be determined in any other suitable manner (e.g., using machine vision, using template matching, using a parametric model, etc.) as described in U.S. patent application Ser. No. 14/072,625. In particular, because variances ($s_i^2$) may be additive for independent samples, Block S140 can calculate the aggregate standard deviation (SD) of the error as a square root of the individual sample variances.

Like Block S130, Block 132 can thus implement a lookup table for estimated blood loss—as described above—to assign specific cEBL bias ($\Delta_i^{cEBL}$) and specific cEBL standard deviation of error ($S_i^{cEBL}$) values to each new surgical textile imaged and analyzed in Blocks S110, S120, and S132.

3.4 Estimated Error: Hemoglobin Mass—Canister

In another implementation, Block S140 calculates a $\Delta_T^{cEHM}$ by summing estimated per-canister biases of all canisters and/or fluid receivers similar to canisters (e.g., suction canister, blood salvage canister, fluid receiving bag, a cell salvage system, a drain device, etc.) imaged and analyzed up to a current point as:

$$\Delta_T^{cEHM} = \Sigma_{i=1}^n \Delta_i^{cEHM},$$

wherein $\Delta_i^{cEHM}$ is the estimated cEHM bias of a canister i, such as specific to the canister type and to a range of EHM values of the canister i.

Block S140 can then calculate a $S_T^{cEHM}$ by summing estimated per-canister SD(error) of all canister images and analyzed up to the current point as:

$$S_T^{cEHM} = \sqrt{\Sigma_{i=1}^n (S_i^{cEHM})^2},$$

wherein $S_i^{cEHM}$ is the estimated cEHM standard deviation of error of the canister i, such as specific to the canister type and a range of EHM values corresponding to the canister i.

As with the surgical textiles, Block S130 can thus implement the lookup table described above to assign $\Delta_i^{cEHM}$ and $S_i^{cEHM}$ values to each new canister imaged and analyzed in Blocks S110, S120, and S130.

3.5 Estimated Error: Whole Blood Volume—Canister

Block S152 can similarly estimate a $\Delta_T^{cEBL}$ of all canisters (e.g., suction canister, blood salvage canister, fluid receiving bag, a cell salvage system, a drain device, etc.) imaged and analyzed up to a current point as:

$$\Delta_T^{cEBL} = \sum_{i=1}^n \frac{\Delta_i^{cEHM}}{Hb_i},$$

wherein $\Delta_i^{cEHM}$ is the cEHM bias of a canister i, such as specific to the canister type and to a range of EHM values of the canister i, and wherein $Hb_i$ is the user-entered estimate of the patient's laboratory derived Hb concentration (e.g., in g/ml or g/dl) corresponding to the time at which canister i was used, as described in U.S. patent application Ser. No. 14/072,625. Additionally or alternatively, $Hb_i$ can be determined in any other suitable manner (e.g., using machine vision, using template matching, using a parametric model, etc.) as described in U.S. patent application Ser. No. 14/072, 625.

Block S152 can further calculate an $S_T^{cEBL}$ as:

$$S_T^{cEBL} = \sqrt{\sum_{i=1}^n \left(\frac{S_i^{cEHM}}{Hb_i}\right)^2},$$

wherein $S_i$ is a standard deviation of a canister i, such as specific to the type of fluid receiver and the predicted cEHM of the canister i. and wherein $Hb_i$ is the user-entered estimate of the patient's laboratory-derived Hb concentration corresponding to the time at which canister i was used (or imaged). Additionally or alternatively, $Hb_i$ can be determined in any other suitable manner (e.g., using machine vision, using template matching, using a parametric model, etc.) as described in U.S. patent application Ser. No. 14/072, 625. In particular, because variances, $s_i^2$, may be additive for independent samples, Block S152 can calculate the aggregate SD of the error as a square root of the individual sample variances.

Like Block S130, Block S132 can thus implement a lookup table for estimated blood loss—as described above— to assign $\Delta_i^{cEBL}$ and $S_i^{cEBL}$ values to each new canister imaged and analyzed in Blocks S110, S120, and S132.

3.6 Estimated Error: Cross Validation

In one variation, a user supplies ground truth values of EHM and EBL for an initial set of fluid receivers (e.g., during a surgery), such as by soaking a sample in saline, wringing fluid output of the sample, centrifuging the bloodied saline, measuring a volume of red blood cells into the centrifuged fluid, and calculating a hemoglobin mass from the volume of red blood cells. In this variation, Blocks S140 and S152 can further implement cross-validation (or other out-of-sample estimate) of error in the cEHM and cEBL values, respectively, for each subsequent fluid receiver based on the ground truth values supplied by the user. For example, Block S140 can implement K-fold cross-validation or 2-fold cross-validation to assess applicability of the lookup table for the corresponding fluid receiver type to the current single fluid receiver or set of fluid receivers, and Block S150 can further present this value to the user.

However, Blocks S140 and S152 can calculate out-of-sample error from an in-vitro (i.e., controlled) setting and/or from clinical study in any other way, and Blocks S140 and S152 can pass these data to Blocks S150 and S162, respectively, for presentation to a user, such as when the user selects or toggles the option at a user interface.

3.7 Estimated Error: Root Mean Square Error

In another variation, Block S140 maintains a running tally of the root mean square error ("$A_{RMS}$," or root mean square deviation) of the aggregate estimated amount of blood component as Blocks S130 and S140 estimate and sum an amount of blood component in each additional fluid receiver. In this variation, Block S140 can thus generate an $A_{RMS}$ that aggregates the magnitude of the bias error (mean differences) and associated standard deviation (differences) values into a single measure of predictive power in units identical to the output variable for estimated amount of blood component (e.g., grams).

Block S140 can calculate an $A_{RMS}$ value at time 't' from an aggregate bias ("$e_T$") and a aggregate variance ($\sigma_T^2$) as:

$$A_{RMS}(t) = \text{sqrt}(\sigma_T^2 + e_T^2).$$

Block S140 can further calculate a $\sigma_T^2$ value and a $e_T$ value of cEHM at time t for each subsequently-imaged fluid receiver by implementing a per-sample variance ("$\sigma_{sample}^2$") and a per-sample bias ("$e_{sample}$") (such as characterized in out-of-sample in-vitro testing or clinical testing) according to:

$$e_T(t) = N(t) \times e_{sample} \text{ and}$$

$$\sigma_T^2(t) = N(t) * \sigma_{sample}^2,$$

wherein N(t) represents a number of fluid receivers scanned at time t (or within a limited time window, such as a two-minute time window) during a current surgical procedure.

Block S152 can similarly maintain a running tally of a root mean square error of the aggregate estimated blood loss as Blocks S132 and S142 estimates and sums a whole blood volume in each additional fluid receiver. Block S152 can thus similarly generate a root mean squared error in units identical to the output variable for estimated blood loss (e.g., milliliters).

4. Providing Data

Figure 3:
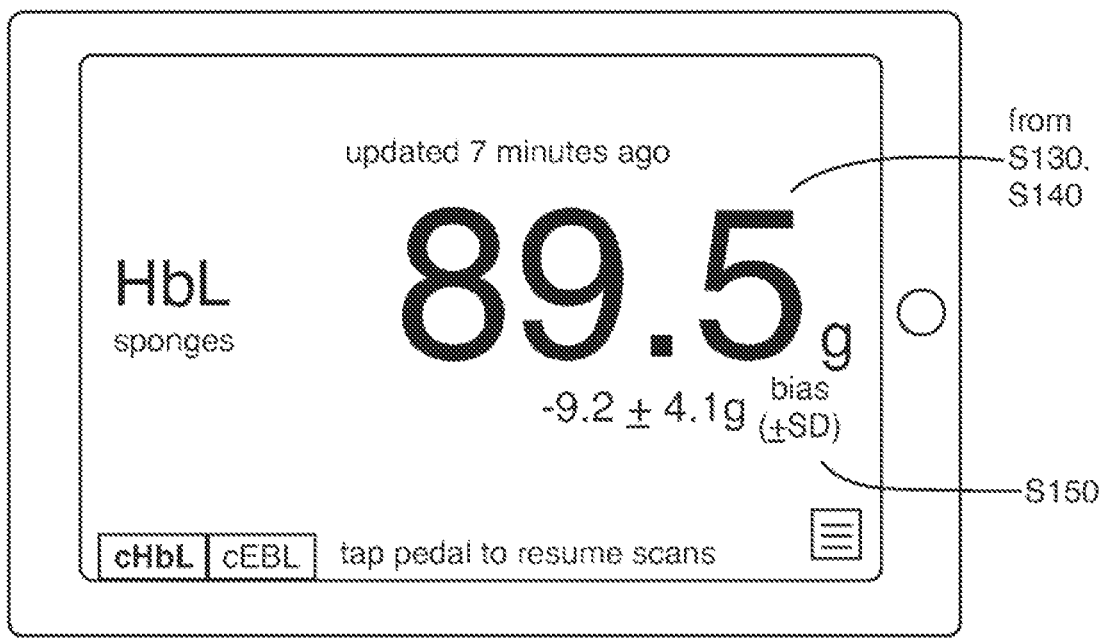
FIG. 3 is a graphical representation of one variation of the method for communicating estimated blood loss parameters of a patient to a user.

As shown in FIGS. 1A, 1B, 1C, and 3, Block S150 of the method recites providing information derived from the aggregate amount of the blood component and the aggregate bias error, from the analysis, to the user. As shown in FIG. 3, in variations, Block S150 of the method recites displaying the aggregate hemoglobin loss of the patient and the aggregate error in the aggregate hemoglobin loss. As shown in FIGS. 2A and 2B, Block S162 similarly recites displaying the aggregate blood loss of the patient and the aggregate error in the aggregate blood loss. Generally, Blocks S150 and S162 can thus function to display estimated biases and/or standard deviations of bias for the values of cEHM and cEBL calculated in Blocks S140 and S152, respectively, thereby providing a user with a more comprehensive view of the accuracy (i.e., bias error) of cEHM and cEBL values calculated from images of fluid receivers. Alternatively, as shown in FIGS. 4A-F, 6, and 8, the user interface can display an estimated amount of a blood or non-blood component and its corresponding bias error—along with the standard deviation of the bias error—as outputted by Block S130 for a single volume of fluid received by a single fluid receiver. For example, Block S162 can display an estimated whole blood volume and its corresponding bias error—along with the standard deviation of the bias error—for a single fluid receiver as output in Block S132. The user interface can also display an aggregate estimated whole blood volume for a set of fluid receivers as output in Block S142.

Blocks S150 and S162 can thus interface with a digital display arranged within an operating room or other surgical setting to render estimated amounts of blood components, associated biases, and standard deviations of biases for a single fluid receiver or an aggregate set of fluid receivers. For example, Blocks S150 and S162 can interface with a digital display of a mobile computing device (e.g., a tablet, a smartphone, etc.) to visually display values calculated in Blocks S130, S132, S140, S142, and/or S152 to a user (e.g., a nurse, an anesthesiologist, etc.). However, Blocks S150 and S162 can present any of these data to a user through any other suitable visual and/or auditory device.

The digital display can further include a user interface, and Blocks S150 and S162 can respond to inputs or mode selections made by a user through the user interface by adjusting a type, a combination, and/or a position of one or more of hemoglobin mass, blood volume, or other blood component along with the calculated bias errors for a current case. Alternatively or in conjunction, the user can adjust a type, combination, and/or a position of one or more types or samples of non-blood components. As shown in FIG. 4F, the user interface can also allow the user to delete individual samples in the calculation of the aggregate estimate amount of a blood or non-blood component as well as its corresponding aggregate bias error. In one example implementation, Blocks 150 and S162 can toggle bias error and standard deviation values of aggregate estimated hemoglobin mass and estimated patient blood loss, respectively, in response to an input into the user interface. In another example implementation, Blocks S150 and S162 toggle through (or between) various sources of error calculated in Blocks S140 and S152, respectively, in response to inputs entered into the user interface by a user, such as according to an error type particularly applicable to a current patient or patient status, a current surgery type, etc. For example, during a surgery on an anemic patient, the user may select an error type that was previously characterized in a study of method accuracy in an anemic patient sample population but later switch to an error type that was characterized in a study of method accuracy in a geriatric patient sample population for a later surgery on a geriatric patient. However, the user may select an error type that corresponds to any combination or number of fluid receiver types, blood component types, patient characteristics, medical procedure characteristics, and/or other suitable types of information. In yet another example implementation, Blocks S150 and/or S162 can display bias error in the estimated amount of blood component across the set of fluid receivers with values for +/−1SD, +/−2SD, +/−3SD, or bias at 95% confidence intervals, etc. based on an error type selected by the user. For example, the aggregate bias error displayed for cEHM can be displayed in the form of calculated Bland-Altman Limits of Agreement as:

$$LOA^{cEHM} = \text{total } cEHM - \Delta_T^{cEHM} \pm 1.96 * S_T^{cEHM}.$$

In another example, the aggregate bias error displayed for cEBL can be displayed in Bland-Altman Limits of Agreement form as:

$$LOA^{cEBL} = \text{total } cEBL - \Delta_T^{cEBL} + 1.96 * S_T^{cEBL}.$$

In another implementation, Blocks S140 and/or S152 further calculate precision-related error bars for the aggregate amount of blood component and the aggregate estimated blood loss values, respectively. Blocks S150 and/or S162 can display these precision-related error bars in conjunction with the corresponding accuracy related bias error (+/−SD) values. Alternatively, in one example, Block S150 can also present the estimated hemoglobin mass in the form of a final output value—such as "150 g"- and error-adjusted values—such as "135 g to 145 g" for a bias of "−10 g" with one standard deviation of "+/−5 g". In a foregoing example, Block S150 can similarly present the data to the user in the form of a bias-compensated estimated amount of blood component—such as in the form of "140 g (130 g to 145 g)." Yet alternatively, Block S150 can display an $A_{RMS}$ value rather than or in addition to an SD value for the bias error in the estimated amount of blood component. Block S162 can implement similar methods or techniques to present aggregate blood loss-related data to the user.

Blocks S150 and S162 can also graph the aggregate estimated amount of blood component and aggregate estimated blood loss of the patient—and the corresponding error values—over time as additional fluid receivers are imaged and analyzed. For example, Block S150 can display a graphical representation of the aggregate estimated hemoglobin mass as a function of time with the bias error (and a standard deviation of the error) calculated in Block S140 following the aggregate estimated hemoglobin mass, such as in the form of: a white dashed line showing cEHM bias and two yellow dashed lines depicting standard deviation of the error on each side of the dashed white line and offset from a solid green line depicting aggregate estimated hemoglobin mass output in Block S140. Blocks S150 and S162 can similarly display a plot of error distribution (e.g., a histogram) relative to the corresponding aggregate estimated hemoglobin mass and aggregate estimate blood loss of the patient, respectively.

Blocks S150 and S162 can also display estimated amounts of blood component and/or related error data in qualitative colors based on a corresponding patient risk level. The method can also trigger an alarm to prompt a user action based on a patient risk level estimated from the aggregate hemoglobin mass and/or aggregate estimated blood loss of the patient, such as described in U.S. patent application Ser. No. 14/072,625.

5. Variations

In a first variation, the method 100 can estimate an amount of a blood component and its associated bias error with respect to multiple volumes of fluid received by multiple fluid receivers captured in a single image. Preferably, the method implements machine vision in order to perform object detection (e.g., finding the pixel coordinates for a bounding box encapsulating the target object) or object segmentation (e.g., finding the pixels that correspond to the target object) for automatically detecting the regions corresponding to the fluid receivers. Alternatively, the regions corresponding to the fluid receivers can be manually detected by, for example, having the user (e.g., a nurse, an anesthesiologist, etc.) spread their fingers on a tap-interface to draw a bounding box around each fluid receiver. The method can perform the object detection, object segmentation, or other region detecting approach using features extracted from a data representation of the image (e.g., pixel values corresponding to color intensities along the red, green, blue (RGB) scale). Preferably, the features are explicitly selected and can include features such as color histograms, histogram of oriented gradients (HOG), scale-invariant feature transform (SIFT), and/or bag-of-words. Alternatively, the features are automatically selected through deep-learning approaches (e.g., recurrent neural networks, convolutional neural networks). Upon detecting the fluid receivers in the image, the method can perform Block S130 to calculate the estimated amounts of the blood component and their associated bias errors in each of the fluid volumes received by each of the fluid receivers. Similarly, the method can perform Block S140 to update the analysis of the aggregate amount of the blood component and the aggregate bias error.

In a first example of the first variation, the image contains multiple types of fluid receivers (e.g., surgical textiles, canisters). In an illustration of the first example, an image contains three fluid receivers: a surgical gauze sponge, a surgical towel, and a suction canister. The method estimates the amounts of blood component—and the associated bias error—in the volumes of fluid for each of the surgical gauze sponge, the surgical towel, and the suction canister. Using the estimates of the amounts of blood component and of the associated bias errors, the method can update the analysis of the aggregate amount of the blood component and the aggregate bias error. Alternatively, Blocks of the method 100 can be performed on images that only contain multiple instances of the same type of fluid receiver, such as an image only containing two suction canisters.

In a second example of the first variation, the method 100 calculates estimated amounts of different types of blood components (e.g., extracorporeal hemoglobin, whole blood, platelet plasma, white blood cells, etc.) for the volumes of fluid received by the fluid receivers. In an illustration of the second example, an image contains two fluid receivers: a surgical gauze sponge and a suction canister. The computing system performs Block S130 to calculate estimated amounts of hemoglobin and platelet content for both the volume of fluid received by the surgical gauze sponge and the volume of fluid received by the suction canister. The computing system can then perform Block S140 to update the analysis of the aggregate amount of the hemoglobin, its associated aggregate bias error, the aggregate amount of the platelet content, and its associated aggregate bias error.

Figure 7:
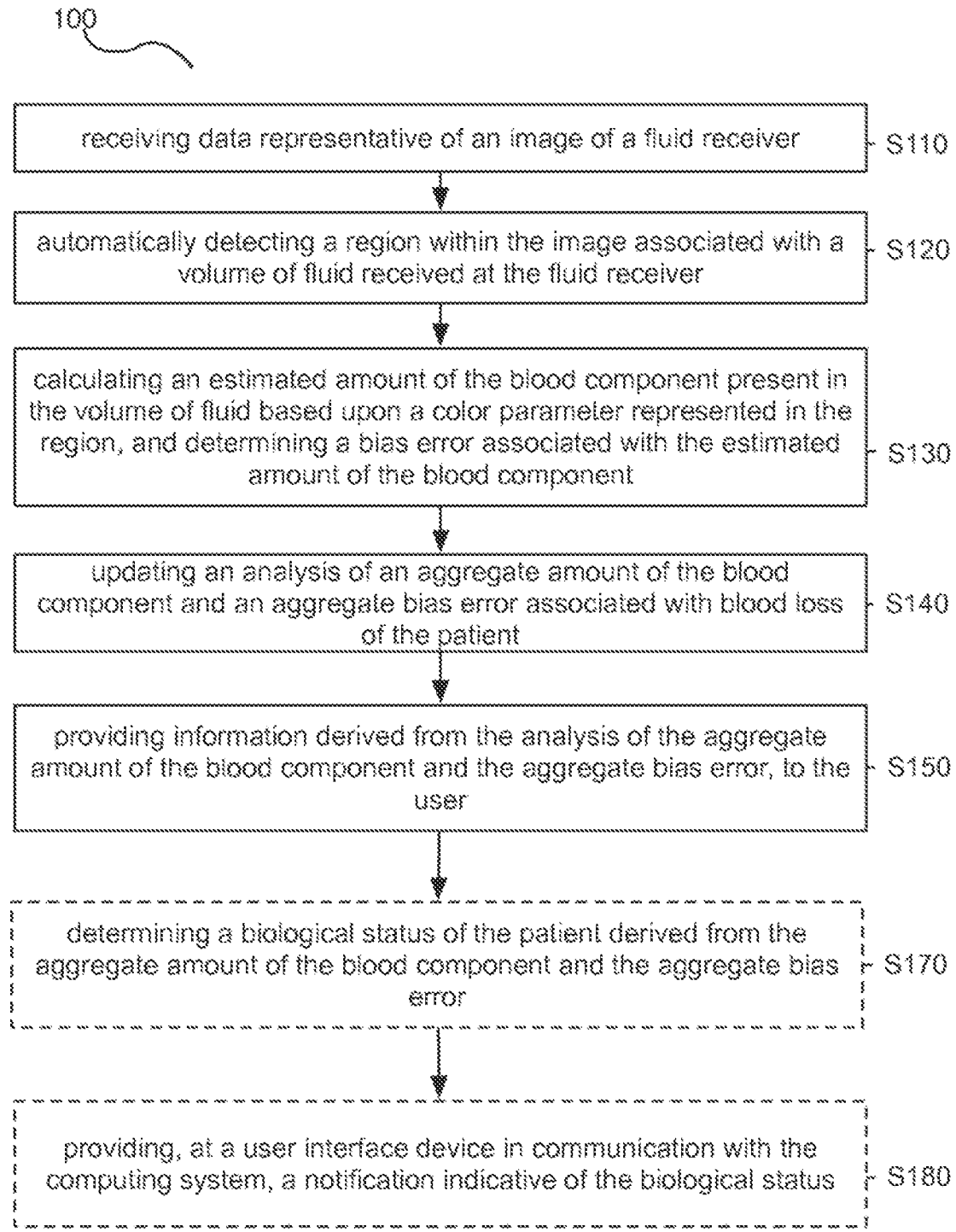
FIG. 7 is a flowchart representation of one variation of the method for communicating estimated blood loss parameters of a patient to a user.
Figure 8:
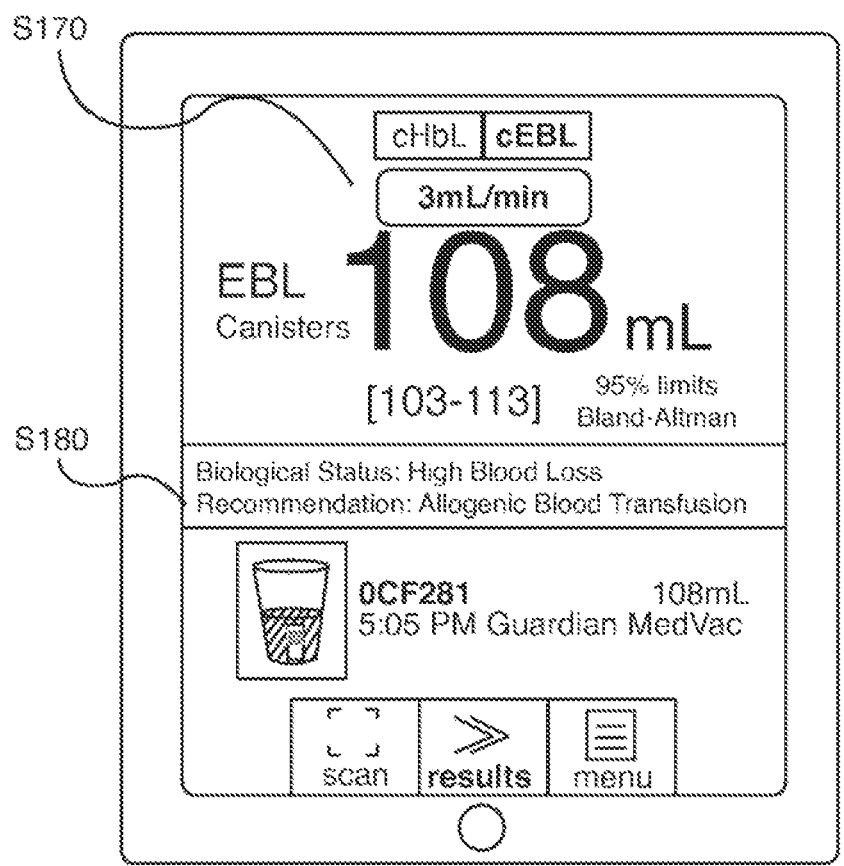
FIG. 8 is a graphical representation of one variation of the method for communicating estimated blood loss parameters of a patient to a user.

As shown in FIGS. 7 and 8, in a second variation, the method further comprises determining a biological status of the patient derived from the aggregate amount of the blood component and the aggregate bias error S170; and providing, at a user interface device in communication with the computing system, a notification indicative of the biological status S180. The method can determine and display a biological status of the patient in terms of actionable recommendations (e.g., "Saline drip recommended") and general statuses (e.g., "Normal blood loss" or "Low plasma concentration"). Preferably, when the biological status comprises an actionable recommendation, the recommendation takes a form that requires no further interpretation (e.g., "Allogeneic blood transfusion recommended"). Alternatively, the actionable recommendations can take a form that requires further medical interpretation upon performance of the recommendation (e.g., "Warning: analyze estimated blood loss"). The determination and display of the biological status is preferably executed continuously in a substantially real-time manner. Alternatively, a patient's biological status can be updated in a more periodic manner, such as upon a manual request inputted by a user (e.g., a nurse, an anesthesiologist, etc.). In Block S180, determination of the patient's biological status preferably is generated from analysis of the aggregate amount of the blood component, the aggregate bias error, and the associated derived information. Alternatively, the biological status can be generated from any of the information resources alone or in combination. Furthermore, in relation to U.S. patent application Ser. No. 14/072,625, Blocks S170 and S180 can be used to monitor a patient's euvolemia status and/or guide responses to changes in the patient's euvolemia status in any suitable manner.

In a first example of the second variation, the computing system determines a patient's blood-related biological status based on an analysis of the aggregate estimated blood loss and associated aggregate bias error. The computing system subsequently communicates the patient's biological status to a user interface that displays and/or notifies the user of the patient's biological status as in Block S18o. In the first example, different biological statuses are determined based on the aggregate volume of estimated blood loss that has occurred over a set period of time. A lookup table can be generated for template matching purposes, the lookup table containing biological statuses (e.g., "Normal amount of blood loss detected") paired to defined ranges of estimated blood loss over time (e.g., 1-1.5 mL/minute). When the aggregate estimated blood loss over time falls into a certain defined range that is defined in the lookup table, the associated biological status is assigned to the patient and displayed to the user. Preferably, the template matching process incorporates the aggregate bias error when examining the lookup table to determine the applicable defined range of values and associated biological status. Alternatively, the settings of the template matching process can be, for example, manually set to assess estimated aggregate blood loss over time without considering the associated aggregate bias error. However, when initially generating the lookup table, aggregate or individual bias errors can be computed for the defined ranges of estimated amount of blood loss over time. In an illustration, a patient undergoing surgery loses 0.7 liters of blood over a length of time that is shorter than expected for the average individual. The computing system examines the lookup table, and determines that the current estimated amount of aggregate blood loss over time falls into a range associated with the biological status of "Allogeneic blood transfusion recommended." The computing system then transmits the patient's biological status to the user interface, which displays the status to the user as in Block S180.

In a second example of the second variation, the computing system determines the patient's biological status based on the information generated in Block S140, Block S150, as well as supplemental situational data. Preferably, supplemental and/or otherwise contextual data comprises patient characteristics (e.g., medical history, genetics, gender, weight, age, height, race, health status, diet, etc.) and medical procedure characteristics (e.g., type of surgery, location of blood loss, localization of blood loss, etc.). In a first illustration of the second example, the computing system determines the patient's biological status through a template matching model using a lookup table as described above. Preferably, different lookup tables can be generated and employed based on the various permutations of the supplemental and/or contextual data (e.g., a situation-specific lookup table can be employed for a 35-year old diabetic patient undergoing cardiac surgery). In a second illustration of the second example, a machine learning model (e.g., supervised, semi-supervised, unsupervised) is employed to classify the patient into a particular biological status. In this illustration, supplemental situational data as well as information generated in Blocks S140 and S150 can be used as features upon which a machine learning classifier (e.g., support vector machines, softmax, linear, non-linear) can be built and trained.

Figure 4A:
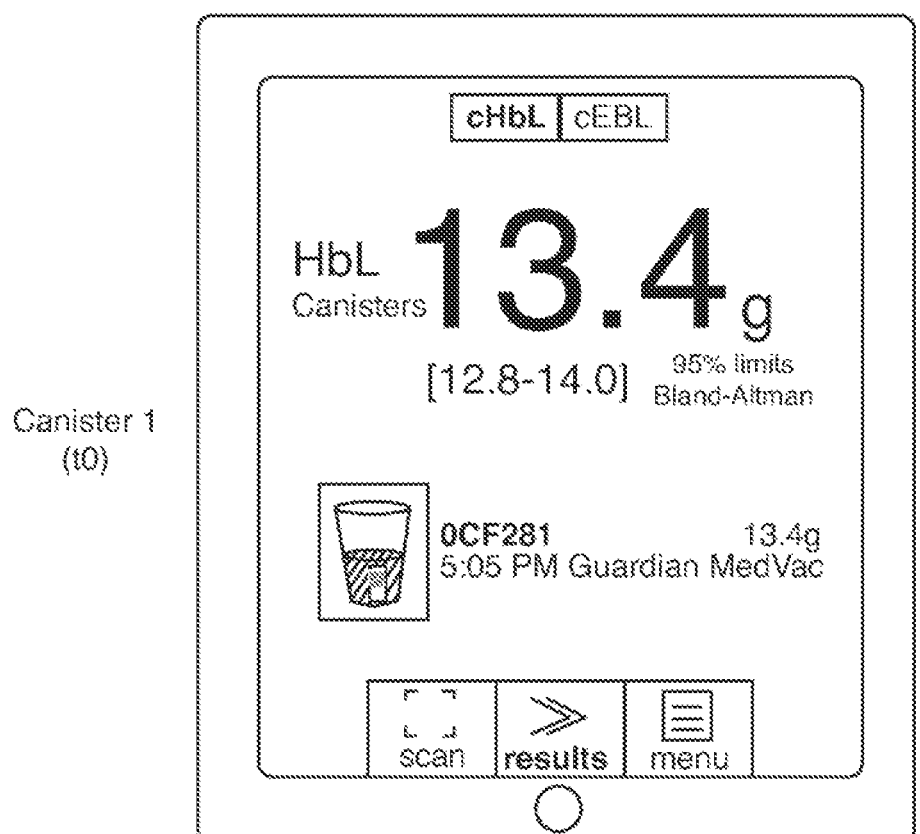
FIGS. 4A-F are graphical representations of one variation of the method for communicating estimated blood loss parameters to a user.
Figure 4B:
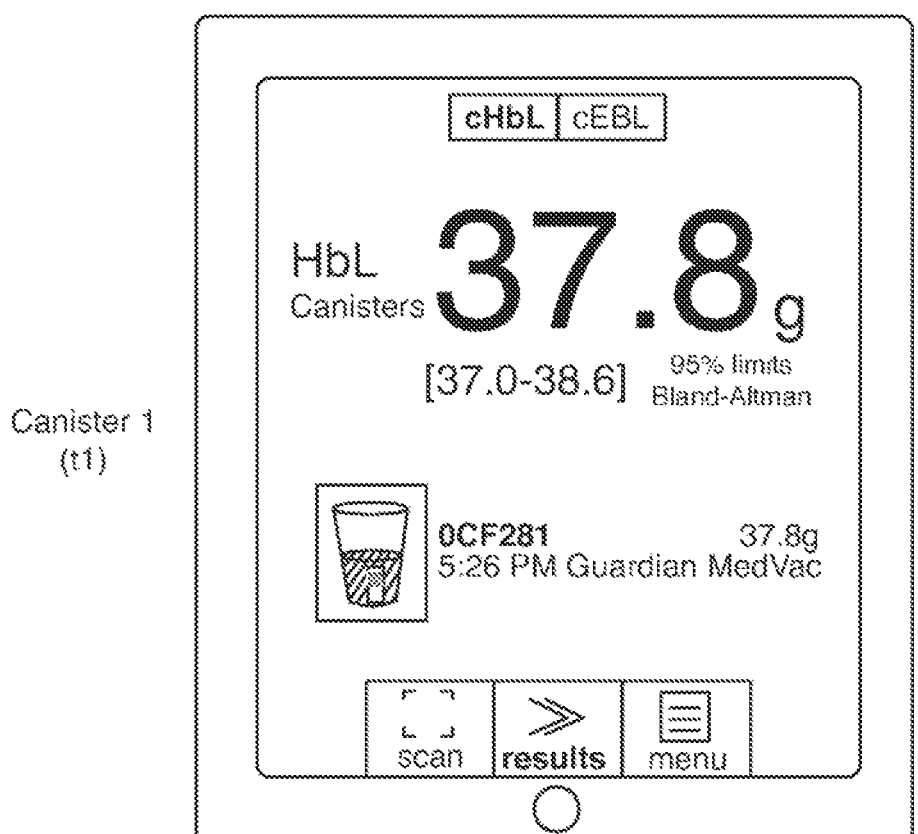
Figure 4C:
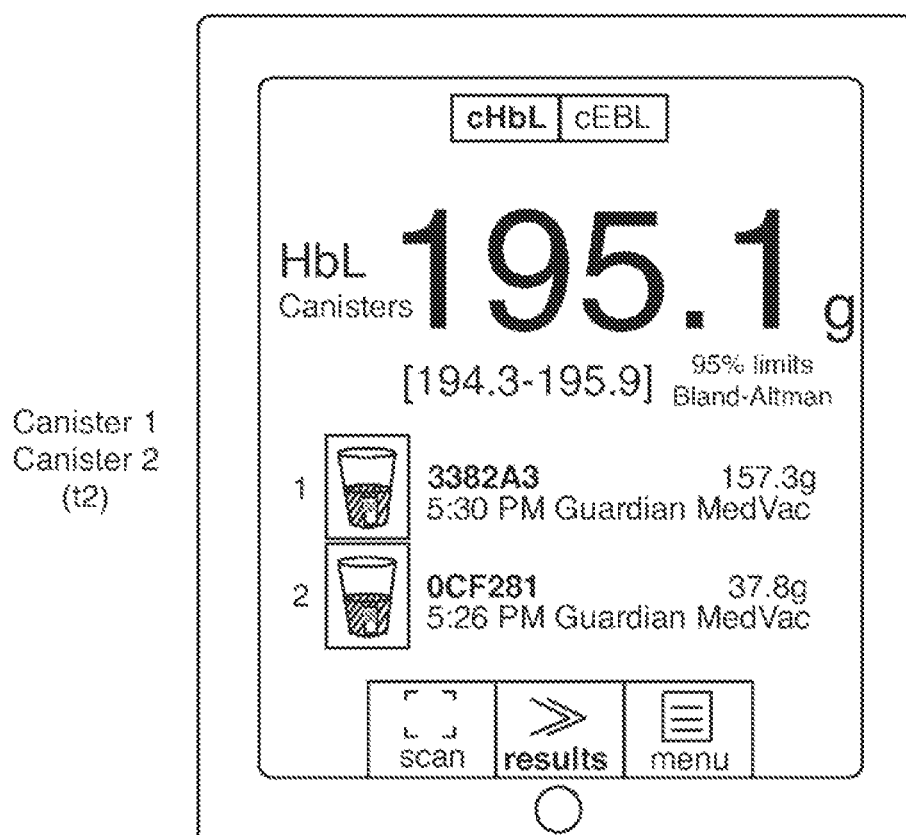
Figure 4D:
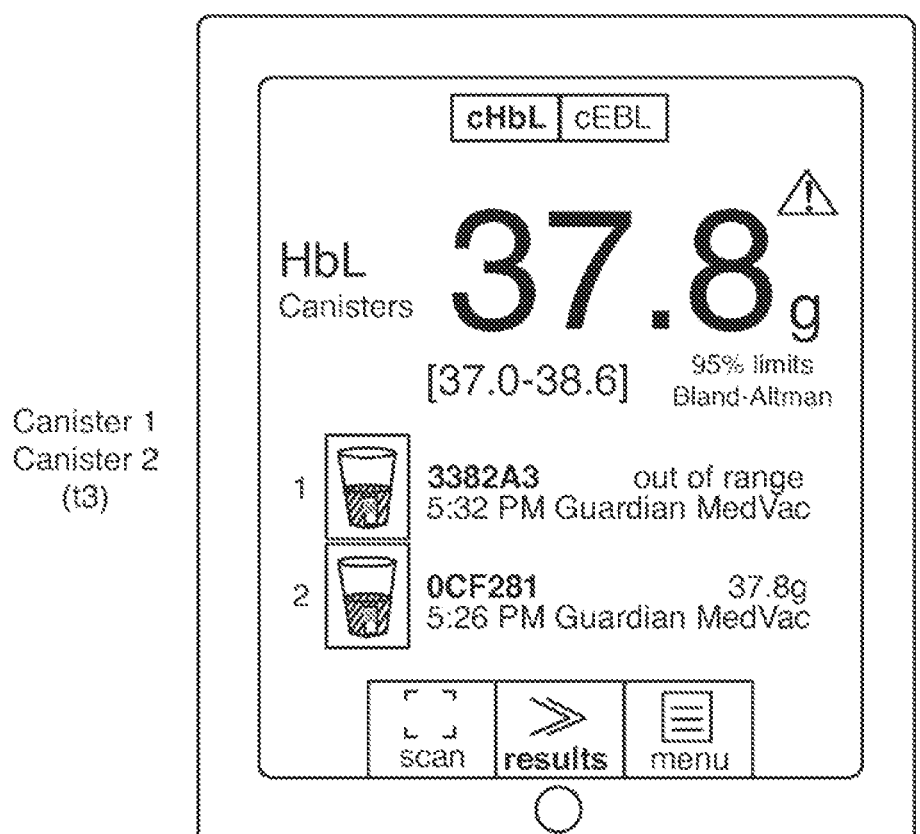
Figure 4E:
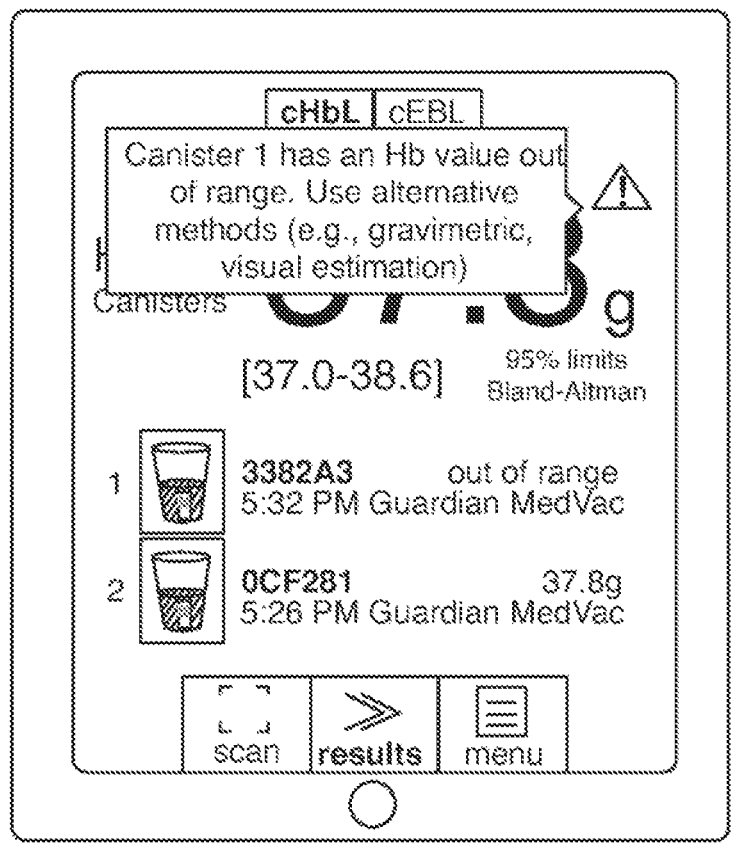
Figure 4F:
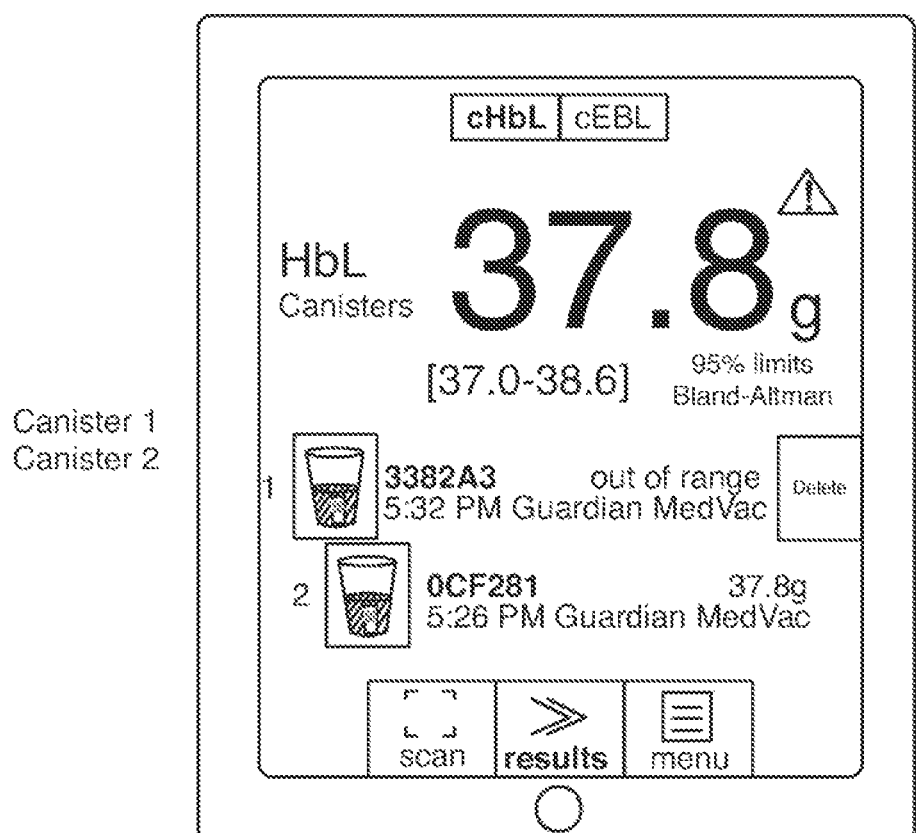
Figure 5:
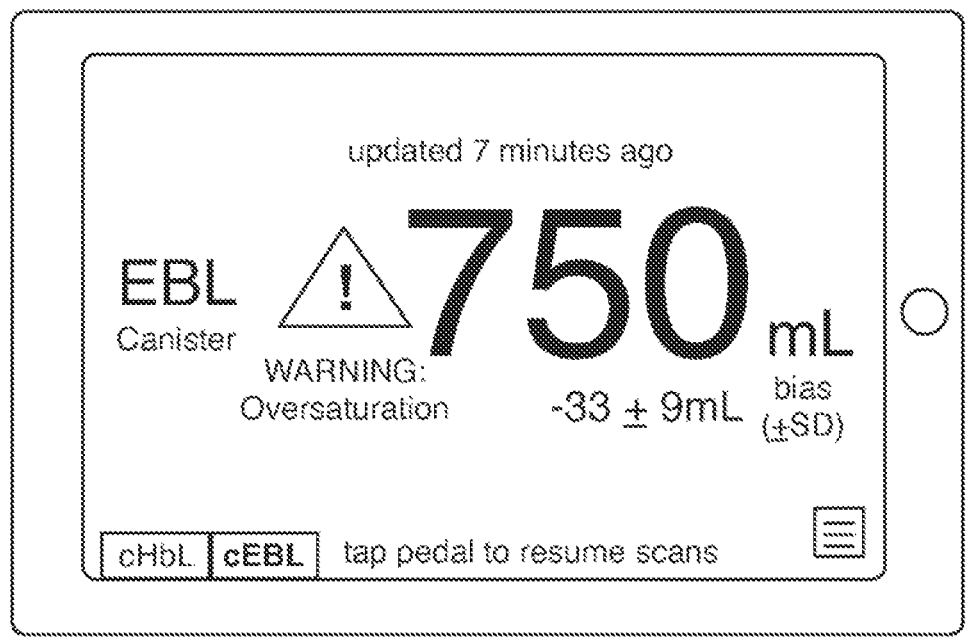
FIG. 5 is a graphical representation of one variation of the method for communicating estimated blood loss parameters of a patient to a user.

As shown in FIGS. 4E and 5, in a third variation, a fluid receiver analyzer status ("analyzer status") notification (e.g., "Unknown fluid receiver type may affect blood component analysis") is provided at a user interface device upon detection that the aggregate or individual amount of blood component and/or the aggregate or individual bias error is outside of a threshold range or amount. In this variation, calculated output values outside a threshold range or amount may indicate that the Blocks of the method 100 were performed under non-ideal conditions, such as when there is an unknown fluid receiver type, insufficient lighting, oversaturation, or poor resolution for captured images. Preferably, the analyzer status notification indicates the conditions that led to the method 100 outputting values outside the threshold range or amount. Alternatively, the analyzer status notification can generally alarm the user that there are non-ideal conditions for blood component analysis. The analyzer status can also indicate a recommendation for the user to perform in order to remedy the conditions (e.g., "Use alternative method such as gravimetric or visual estimation"). In examples, the analyzer status notification comes in the form of a visual alert (e.g., a pop up on the user interface, non-verbal symbol or image, alert with words or sentences). In other examples, the notification comes in the form of a vibration (e.g., the user interface device vibrates). However, the notification can come in any suitable form (e.g., auditory, touch-based, haptic, etc.). Preferably, the user is automatically notified when the computing system identifies that the outputted values are outside the threshold range or amount. However, the user can also be notified based off of manually set user configurations and inputs (e.g., a user can set their own threshold ranges or amounts)

In another variation, the method 100 can estimate an amount of a blood component and/or non-blood component and its associated bias error with respect to volumes of fluid associated with fluid receivers that are intracorporeal (i.e., situated or occurring within the body). Preferably, the intracorporeal fluid receivers are biological components such as organs, tissues, or cells. Alternatively, the intracorporeal fluid receivers can be non-biological such as a medical device, an implant, or other non-biological component found within the body. In this variation, the method can estimate an amount of a blood component and its associated bias errors from images of fluid receivers in their intracorporeal state while still situated or found within the body. Alternatively, the method can estimate an amount of a blood component and its associated bias errors from images of intracorporeal fluid receivers that have been excised or removed from the patient's body. In an illustration, the computing system calculates an estimated amount of blood component and its associated error with respect to a patient's tissue that a medical professional excised during surgery.

As described above, the method 100 can calculate and present to a user aggregate error for a biometric value monitored during a surgery or other clinical effect, such as aggregate estimated patient blood loss estimated from a sum of blood volume estimates for individual fluid receivers over time. However, in another variation, the method can also calculate error in non-aggregate biometric measurements. For example, the method can implement similar techniques to estimate and share with a user an error in a real-time hematocrit estimate of a patient or an error in a patient blood oxygen saturation measured with a non-invasive pulse oximeter.

As shown in FIGS. 4A-4D, in another variation, the method tracks hemoglobin mass, whole blood volume, and/or an amount of another blood component and the corresponding non-cumulating error values of an accumulating parameter. For example, the method can estimate hemoglobin mass and aggregate blood volume contained in a surgical suction canister as the canister fills with patient and irrigation fluids over time as well as corresponding errors each time, such as for each instance that the method extrapolates a hemoglobin mass and/or a whole blood volume from an image of the canister (e.g., at a sample rate of 1 Hz). Thus, the method can implement techniques as described above to calculate blood-related quantities and related error values for a parameter that is not aggregate (i.e., not a compilation of multiple discrete quantities and associated errors) but is inherently aggregate in its contents.

However, the method 100 can be applied to any other measured and/or monitored biometric parameter to calculate a patient-related value, to calculate an error associated with the patient-related value, and to present the data to a user.

The systems and methods of the preferred embodiment can be embodied and/or implemented at least in part as a machine configured to receive a computer-readable medium storing computer-readable instructions. The instructions are preferably executed by computer-executable components preferably integrated with the application, applet, host, server, network, website, communication service, communication interface, hardware/firmware/software elements of a user computer or mobile device, or any suitable combination thereof. Other systems and methods of the preferred embodiment can be embodied and/or implemented at least in part as a machine configured to receive a computer-readable medium storing computer-readable instructions. The instructions are preferably executed by computer-executable components preferably integrated by computer-executable components preferably integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component is preferably a processor but any suitable dedicated hardware device can (alternatively or additionally) execute the instructions.

As a person skilled in the art will recognize from the previous detailed description and from the figures and claims, modifications and changes can be made to the preferred embodiments of the invention without departing from the scope of this invention as defined in the following claims.

We claim:

1. A method comprising:
    accessing, by one or more processors, an image including a representation of a fluid receiver having fluid from a patient, the fluid including a blood component;

identifying, by the one or more processors, that the fluid receiver in the image is of a specific type;

detecting, by the one or more processors, a region in the image that is within the fluid receiver and includes the fluid;

determining, by the one or more processors, an amount of the blood component in the fluid receiver and a corresponding error, based on the region and the specific type of fluid receiver; and providing, by the one or more processors, information based on the determined amount of the blood component and the corresponding error, to a user.

2. The method of claim 1, further comprising:

accessing, by the one or more processors, a second image including a representation of a second fluid receiver;

identifying, by the one or more processors, that the second fluid receiver is of a second type, the second type being different from the specific type;

detecting, by the one or more processors, a region in the second image that is within the second fluid receiver and includes the fluid;

determining, by the one or more processors, a second amount of the blood component in the second fluid receiver based on the region in the second image and the second type of fluid receiver, and a corresponding second error; and updating the provided information based on the determined second amount of the blood component and on the corresponding second error.

3. The method of claim 2, wherein the specific type of the fluid receiver is a surgical textile and the second type of the second fluid receiver is a container.

4. The method of claim 1, further comprising:

identifying, by the one or more processors, that a second fluid receiver represented in the image is of a second type, the second type being different from the specific type;

detecting, by the one or more processors, a second region in the image that is within the second fluid receiver and includes the fluid;

determining, by the one or more processors, a second amount of the blood component in the second fluid receiver based on the second region and the second type of fluid receiver, and a corresponding second error; and updating the provided information based on the determined second amount of the blood component and on the corresponding second error.

5. The method of claim 1, further comprising:

updating, by the one or more processors, an analysis of an aggregate amount of the blood component and an aggregate error associated with the blood component of the patient, based upon the amount of the blood component and the corresponding error, wherein the provided information is derived from the analysis of the aggregate amount of the blood component and the aggregate error.

6. The method of claim 5 further comprising:

determining, by the one or more processors, that either the aggregate amount of the blood component or the aggregate error has exceeded a threshold; and providing, by the one or more processors, a notification that the threshold has been exceeded.

7. The method of claim 1 further comprising:

determining, by the one or more processors, an estimated blood loss volume within the fluid receiver and a corresponding blood loss volume error, based on the region and the specific type; and providing, by the one or more processors, information based on the estimated blood loss volume and the corresponding blood loss volume error, to a user.

8. The method of claim 7, wherein:

the determined amount of the blood component includes an estimated quantity of hemoglobin in the fluid included in the fluid receiver; and the determined corresponding error includes an error in the estimated quantity of hemoglobin.

9. The method of claim 7, further comprising:

updating, by the one or more processors, an analysis of an aggregate amount of the blood component and an aggregate error associated with the blood component of the patient, based upon the amount of the blood component and the corresponding error; and updating, by the one or more processors, an analysis of an aggregate amount of the estimated blood loss volume and an aggregate error associated with the blood loss volume of the patient, based on the estimated blood loss volume and the corresponding blood loss volume error, wherein the provided information is derived from the analysis of the aggregate amount of the blood component, the aggregate error associated with the blood component, aggregate amount of the estimated blood loss volume and an aggregate error associated with the blood loss volume.

10. A computer system comprising:

one or more processors; and a memory storing instructions that, when executed by the one or more processors, configure the computer system to performing operations comprising:

accessing an image including a representation of a fluid receiver having fluid from a patient, the fluid including a blood component;

identifying that the fluid receiver in the image is of a specific type;

detecting a region in the image that is within the fluid receiver and includes the fluid;

determining an amount of the blood component in the fluid receiver and a corresponding error, based on the region and the specific type of fluid receiver; and providing information based on the determined amount of the blood component and the corresponding error, to a user.

11. The computer system of claim 10, wherein the operations further comprise:

accessing a second image including a representation of a second fluid receiver;

identifying that the second fluid receiver is of a second type, the second type being different from the specific type;

detecting a region in the second image that is within the second fluid receiver and includes the fluid;

determining a second amount of the blood component in the second fluid receiver based on the region in the second image and the second type of fluid receiver, and a corresponding second error; and updating the provided information based on the determined second amount of the blood component and on the corresponding second error.

12. The computer system of claim 11, wherein the specific type of the fluid receiver is a surgical textile and the second type of the second fluid receiver is a container.

13. The computer system of claim 10, wherein the operations further comprise:

identifying that a second fluid receiver represented in the image is of a second type, the second type being different from the specific type;

detecting a second region in the image that is within the second fluid receiver and includes the fluid;

determining a second amount of the blood component in the second fluid receiver based on the second region and the second type of fluid receiver, and a corresponding second error; and updating the provided information based on the determined second amount of the blood component and on the corresponding second error.

14. The computer system of claim 10, wherein the operations further comprise:

updating an analysis of an aggregate amount of the blood component and an aggregate error associated with the blood component of the patient, based upon the amount of the blood component and the corresponding error, wherein the provided information is derived from the analysis of the aggregate amount of the blood component and the aggregate error.

15. The computer system of claim 10, wherein the operations further comprise:

determining an estimated blood loss volume within the fluid receiver and a corresponding blood loss volume error, based on the region and the specific type; and providing information based on the estimated blood loss volume and the corresponding blood loss volume error, to a user.

16. A non-transitory computer-readable storage medium, the computer-readable storage medium including instructions that when executed by a computer system, cause the computer system to performing operations comprising:

accessing an image including a representation of a fluid receiver having fluid from a patient, the fluid including a blood component;

identifying that the fluid receiver in the image is of a specific type;

detecting a region in the image that is within the fluid receiver and includes the fluid;

determining an amount of the blood component in the fluid receiver and a corresponding error, based on the region and the specific type of fluid receiver; and providing information based on the determined amount of the blood component and the corresponding error, to a user.

17. The computer-readable storage medium of claim 16, wherein the operations further comprise:

accessing a second image including a representation of a second fluid receiver;

identifying that the second fluid receiver is of a second type, the second type being different from the specific type;

detecting a region in the second image that is within the second fluid receiver and includes the fluid;

determining a second amount of the blood component in the second fluid receiver based on the region in the second image and the second type of fluid receiver, and a corresponding second error; and updating the provided information based on the determined second amount of the blood component and on the corresponding second error.

18. The computer-readable storage medium of claim 16, wherein the operations further comprise:

updating an analysis of an aggregate amount of the blood component and an aggregate error associated with the blood component of the patient, based upon the amount of the blood component and the corresponding error, wherein the provided information is derived from the analysis of the aggregate amount of the blood component and the aggregate error.

19. The computer-readable storage medium of claim 16 wherein the operations further comprise:

determining an estimated blood loss volume within the fluid receiver and a corresponding blood loss volume error, based on the region and the specific type; and providing information based on the estimated blood loss volume and the corresponding blood loss volume error, to a user.

20. The computer-readable storage medium of claim 19, wherein the operations further comprise:

updating an analysis of an aggregate amount of the blood component and an aggregate error associated with the blood component of the patient, based upon the amount of the blood component and the corresponding error;

updating an analysis of an aggregate amount of the estimated blood loss volume and an aggregate error associated with the blood loss volume of the patient, based on the estimated blood loss volume and the corresponding blood loss volume error, wherein the provided information is derived from the analysis of the aggregate amount of the blood component, the aggregate error associated with the blood component, aggregate amount of the estimated blood loss volume and an aggregate error associated with the blood loss volume.

* * * * *